US012594129B2

(12) United States Patent
Richmond et al.

(10) Patent No.: US 12,594,129 B2
(45) Date of Patent: Apr. 7, 2026

(54) TRACKABLE RETRACTOR SYSTEMS, APPARATUSES, DEVICES, AND METHODS

(71) Applicant: SYNAPTIVE MEDICAL INC., Toronto (CA)

(72) Inventors: Joshua Lee Richmond, Toronto (CA); Gal Sela, Toronto (CA)

(73) Assignee: Synaptive Medical Inc.

( * ) Notice: Subject to any disclaimer, the term of this patent is extended or adjusted under 35 U.S.C. 154(b) by 336 days.

(21) Appl. No.: 18/300,471

(22) Filed: Apr. 14, 2023

(65) Prior Publication Data

US 2023/0329804 A1 Oct. 19, 2023

Related U.S. Application Data

(60) Provisional application No. 63/363,053, filed on Apr. 15, 2022.

(51) Int. Cl.
| | |
|---|---|
| *A61B 34/20* | (2016.01) |
| *A61B 17/02* | (2006.01) |
| *A61B 90/50* | (2016.01) |
| *A61B 17/00* | (2006.01) |
| *A61B 90/00* | (2016.01) |

(52) U.S. Cl.
CPC .......... *A61B 34/20* (2016.02); *A61B 17/0206* (2013.01); *A61B 90/50* (2016.02); *A61B 2017/00203* (2013.01); *A61B 2017/00477* (2013.01); *A61B 2034/2055* (2016.02); *A61B 2034/2072* (2016.02); *A61B 2090/3945* (2016.02)

(58) Field of Classification Search
None
See application file for complete search history.

(56) References Cited

U.S. PATENT DOCUMENTS

| | | | | |
|---|---|---|---|---|
| 7,416,553 | B2 * | 8/2008 | Patel .................. | A61B 17/1757 |
| | | | | 606/246 |
| 2003/0088157 | A1 * | 5/2003 | Vassiliades, Jr. .. | A61B 17/0206 |
| | | | | 600/202 |
| 2017/0304009 | A1 * | 10/2017 | Kheradpir ............ | A61M 1/7411 |
| 2020/0360100 | A1 * | 11/2020 | Mantri .................. | A61B 90/37 |

* cited by examiner

*Primary Examiner* — Tessa M Matthews

(57) ABSTRACT

Trackable retractor systems, apparatuses, devices, and methods involving: retractor blades, each retractor blade having a proximal end and a distal end, the retractor blades having a blade axis defined by a midline therebetween or thereamong; actuation arms, each actuation arm having a proximal end and a distal end, each actuation arm distal end configured to correspondingly couple with each retractor blade proximal end, and each actuation arm configured to correspondingly actuate each retractor blade; a positioning arm configured to position each actuation arm; a movable clamp configured to movably couple with the positioning arm and one actuation arm and to move the one actuation arm relative to another actuation arm; and three distinct tracking features disposed in a tracking plane, two distinct tracking features configured to correspondingly couple with the retractor blade proximal ends, one other distinct tracking feature configured to couple with the movable clamp, and each distinct tracking feature having a distinct tracking token, whereby the blade axis is maintained in a position orthogonal to the tracking plane, and whereby optical alignment is maintained along the blade axis in relation to a desired focal depth.

12 Claims, 12 Drawing Sheets

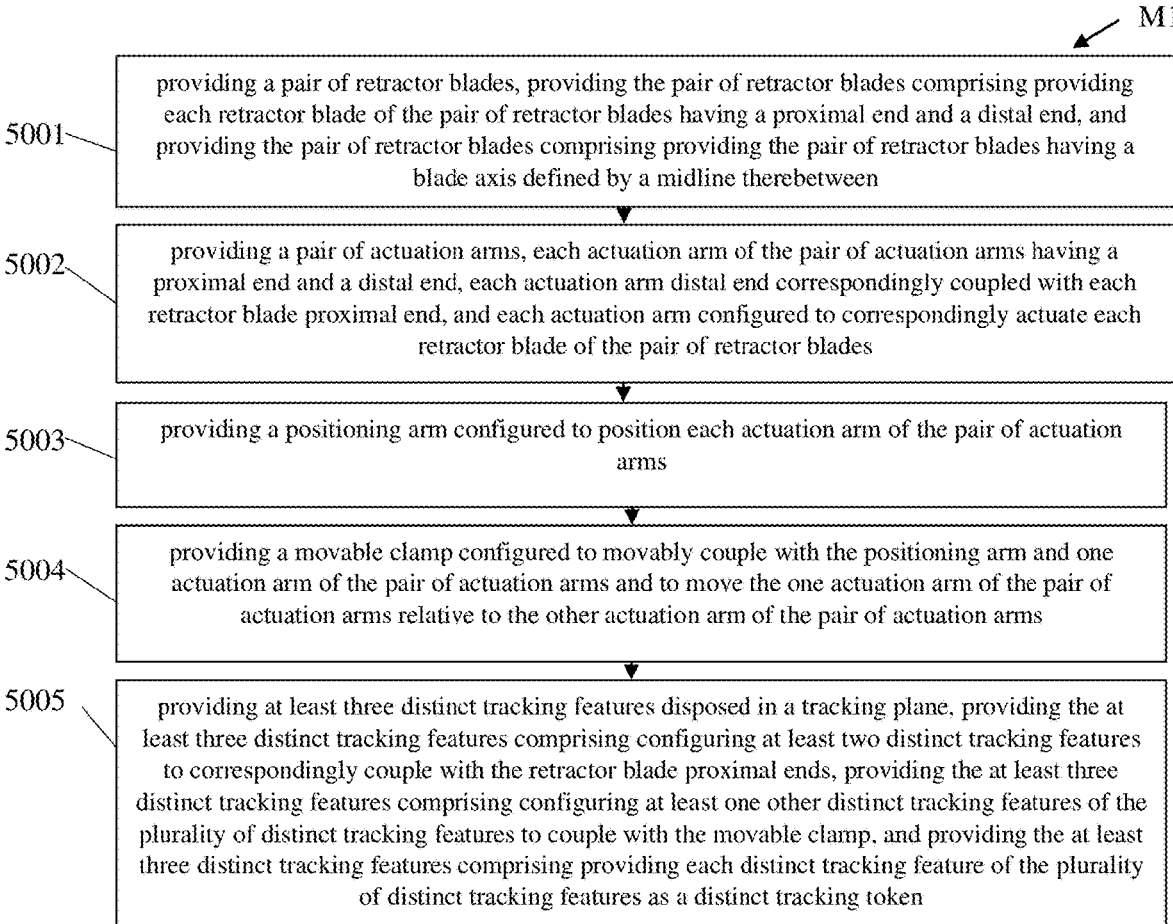

5001 — providing a pair of retractor blades, providing the pair of retractor blades comprising providing each retractor blade of the pair of retractor blades having a proximal end and a distal end, and providing the pair of retractor blades comprising providing the pair of retractor blades having a blade axis defined by a midline therebetween 5002 — providing a pair of actuation arms, each actuation arm of the pair of actuation arms having a proximal end and a distal end, each actuation arm distal end correspondingly coupled with each retractor blade proximal end, and each actuation arm configured to correspondingly actuate each retractor blade of the pair of retractor blades 5003 — providing a positioning arm configured to position each actuation arm of the pair of actuation arms 5004 — providing a movable clamp configured to movably couple with the positioning arm and one actuation arm of the pair of actuation arms and to move the one actuation arm of the pair of actuation arms relative to the other actuation arm of the pair of actuation arms 5005 — providing at least three distinct tracking features disposed in a tracking plane, providing the at least three distinct tracking features comprising configuring at least two distinct tracking features to correspondingly couple with the retractor blade proximal ends, providing the at least three distinct tracking features comprising configuring at least one other distinct tracking features of the plurality of distinct tracking features to couple with the movable clamp, and providing the at least three distinct tracking features comprising providing each distinct tracking feature of the plurality of distinct tracking features as a distinct tracking token

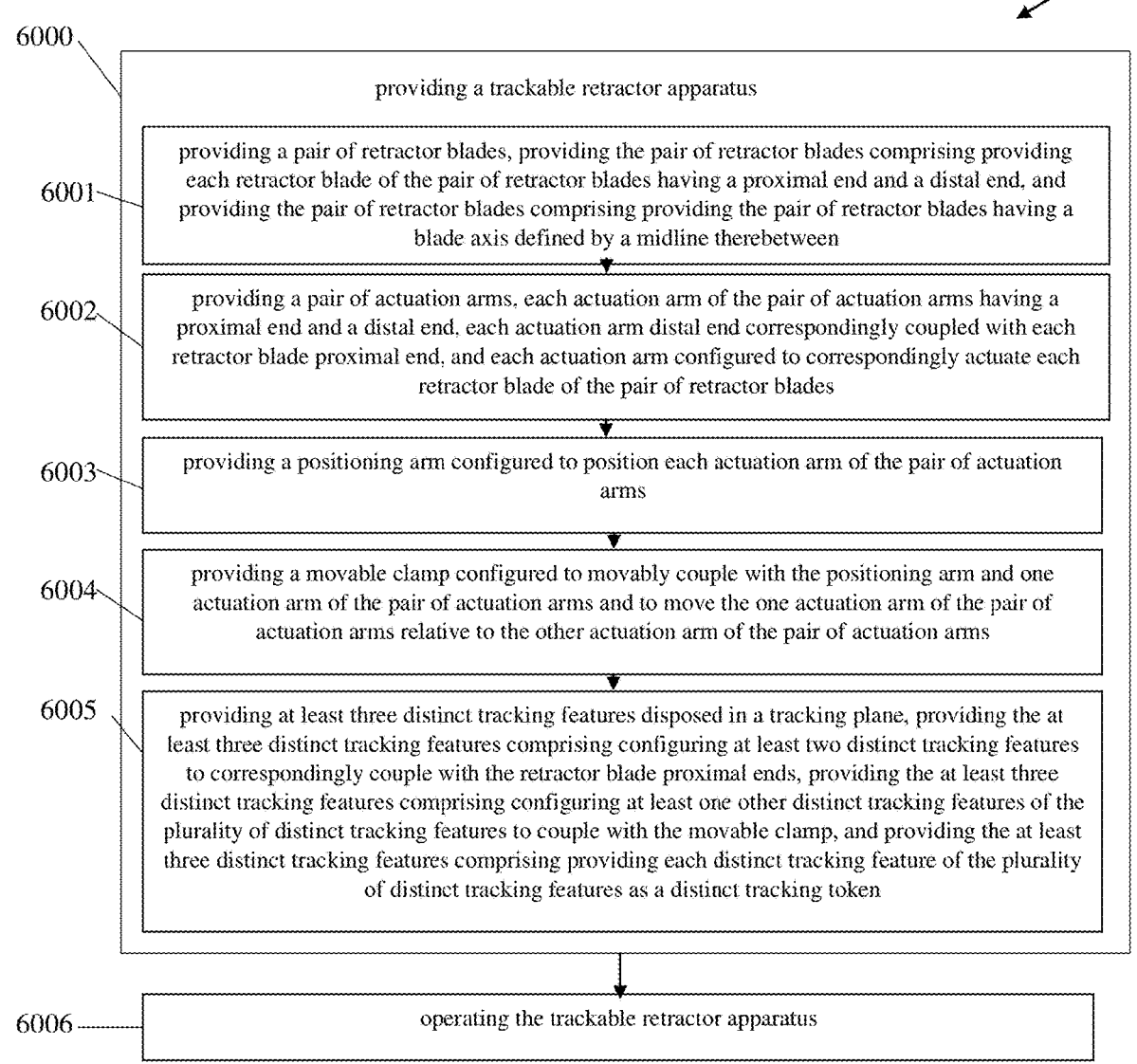

6000 providing a trackable retractor apparatus

6001 providing a pair of retractor blades, providing the pair of retractor blades comprising providing each retractor blade of the pair of retractor blades having a proximal end and a distal end, and providing the pair of retractor blades comprising providing the pair of retractor blades having a blade axis defined by a midline therebetween

6002 providing a pair of actuation arms, each actuation arm of the pair of actuation arms having a proximal end and a distal end, each actuation arm distal end correspondingly coupled with each retractor blade proximal end, and each actuation arm configured to correspondingly actuate each retractor blade of the pair of retractor blades

6003 providing a positioning arm configured to position each actuation arm of the pair of actuation arms

6004 providing a movable clamp configured to movably couple with the positioning arm and one actuation arm of the pair of actuation arms and to move the one actuation arm of the pair of actuation arms relative to the other actuation arm of the pair of actuation arms

6005 providing at least three distinct tracking features disposed in a tracking plane, providing the at least three distinct tracking features comprising configuring at least two distinct tracking features to correspondingly couple with the retractor blade proximal ends, providing the at least three distinct tracking features comprising configuring at least one other distinct tracking features of the plurality of distinct tracking features to couple with the movable clamp, and providing the at least three distinct tracking features comprising providing each distinct tracking feature of the plurality of distinct tracking features as a distinct tracking token

6006 operating the trackable retractor apparatus

FIG. 12

TRACKABLE RETRACTOR SYSTEMS, APPARATUSES, DEVICES, AND METHODS

CROSS REFERENCE TO RELATED APPLICATIONS

The present disclosure claims priority to and the benefit of U.S. Utility Patent Application Ser. No. 63/363,053, entitled "TRACKABLE RETRACTOR SYSTEMS, APPARATUSES, DEVICES, AND METHODS", filed on Apr. 15, 2022, the disclosure of which are incorporated herein by reference in their entirety. for optical imaging.

FIELD

The present disclosure generally relates to technologies for tracking retractor apparatuses. More specifically, the present disclosure relates to technologies for tracking retractor apparatuses using tracking systems for optical imaging.

BACKGROUND

In the related art, retractors are typically used to hold an incision or a wound in an open position while a surgeon works. Related art retractors are also typically used to hold tissue or organs away from a surgical site during surgery. Some related art retractors involve self-retaining retractors that allow hands-free operation during surgery. Other related art retractors involve opposing blades having a screw, a ratchet, or a clamp for holding apart the tissue without manual assistance and are referred as self-retaining retractors. Some related art retractors involve the use of indistinct tracking markers.

also in the related art, surgical microscopes are typically used in conjunction with retractors during surgical procedures to provide a detailed or magnified view of the surgical site. In some cases, separate narrow field and wide field scopes are used within the same surgical procedure to obtain image views with different zoom ranges. Often, adjusting the zoom and the focus of such a surgical microscope requires the user, e.g., a surgeon, to manually adjust the optics of the microscope, such as when the optical pathway becomes unaligned with the retractor, which is difficult, time-consuming, and frustrating, particularly during a surgical procedure. Challenges experienced by these related art retractors include an inability to self-correct their positions during surgery. Therefore, a long-felt need exists in the related art for providing solutions to these challenges.

SUMMARY

In addressing at least the related art challenges, the subject matter of the present disclosure provides trackable retractor systems, apparatuses, devices, and methods, involving: a pair of retractor blades, each retractor blade of the pair of retractor blades having a proximal end and a distal end, the pair of retractor blades having a blade axis defined by a midline therebetween; a pair of actuation arms, each actuation arm of the pair of actuation arms having a proximal end and a distal end, each actuation arm distal end configured to correspondingly couple with each retractor blade proximal end, and each actuation arm configured to correspondingly actuate each retractor blade of the pair of retractor blades; a positioning arm configured to position each actuation arm of the pair of actuation arms; a movable clamp configured to movably couple with the positioning arm and one actuation arm of the pair of actuation arms and to move the one actuation arm of the pair of actuation arms relative to the other actuation arm of the pair of actuation arms; and at least three distinct tracking features disposed in a tracking plane, at least two distinct tracking features of the at least three distinct tracking features configured to correspondingly couple with the retractor blade proximal ends, at least one other distinct tracking feature of the plurality of distinct tracking features configured to couple with the movable clamp, and each distinct tracking feature of the plurality of distinct tracking features having a distinct tracking token, whereby the blade axis is maintained in a position orthogonal to the tracking plane, and whereby optical alignment is maintained along the blade axis in relation to a desired focal depth.

BRIEF DESCRIPTION OF THE DRAWING(S)

Reference is made, by way of example(s), to the accompanying Drawing(s) which illustrate example embodiments of the present disclosure, wherein similar reference numerals may be used in the several figures of the Drawing(s) to denote similar components, and wherein:

FIG. 11 is a flow diagram illustrating a method of providing a trackable retractor apparatus, as shown in FIG. 10, usable with the control and processing system, as shown in FIG. 4, during a medical procedure, such as a surgical procedure, as shown in FIG. 5, and an image-guided surgical procedure;

FIG. 12 is a flow diagram illustrating a method of maintaining optical alignment by way of a trackable retractor apparatus, as shown in FIG. 10, usable with the control and processing system, as shown in FIG. 4, during a medical procedure, such as a surgical procedure, as shown in FIG. 5, and an image-guided surgical procedure;

Figure 1:
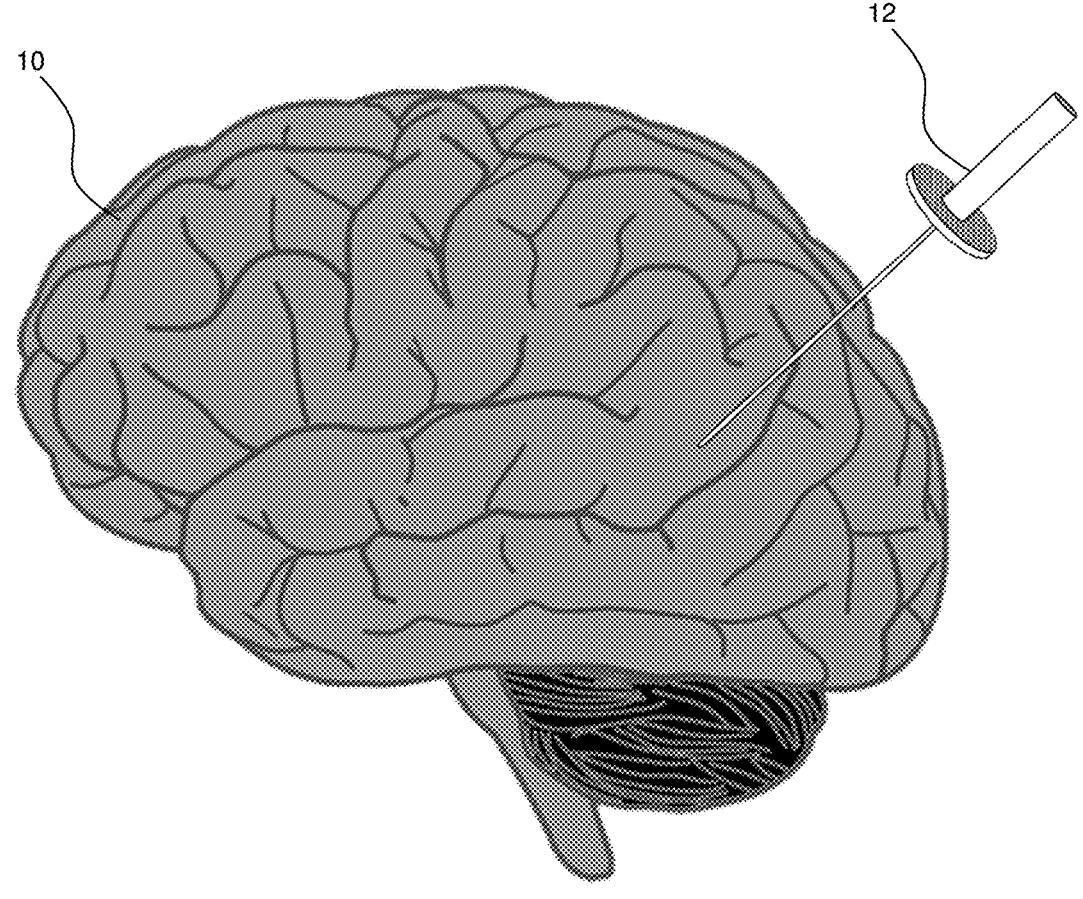
FIG. 1 is a diagram illustrating an access port inserted into a brain, such as a human brain, the access port providing access to internal tissue of the brain during a medical procedure.

Corresponding reference numerals or characters indicate corresponding components throughout the several figures of the Drawing(s). Elements in the several figures of the Drawing(s) are illustrated for simplicity and clarity and have not necessarily been drawn to scale. For example, the dimensions of some elements in the several figures may be emphasized relative to other elements for facilitating understanding of the various presently disclosed embodiments. Also, common, but well-understood, elements that are useful or necessary in a commercially feasible embodiment are often not depicted to facilitate a less obstructed view of these various embodiments of the present disclosure.

DETAILED DESCRIPTION

Various embodiments and aspects of the present disclosure are below described with details. The following description and the appended drawings are illustrative of the present disclosure and are not to be construed as limiting the present disclosure. Numerous specific details are described to provide a thorough understanding of various embodiments of the present disclosure. However, in certain instances, well-known or conventional details are not described to provide a concise discussion of the embodiments of the present disclosure.

The systems and methods herein described are useful in image guided medical procedures, such as procedures in the field of spinal surgery or in the field of neurosurgery, e.g., including oncological care, neurodegenerative disease, stroke, brain trauma, and orthopedic surgery. The teachings of the present disclosure are applicable to other conditions or fields of medicine. While the present disclosure describes examples in the context of neurosurgery, the present disclosure is also applicable to other surgical procedures that use intraoperative optical imaging.

Various example apparatuses or processes are below described. No example embodiment below described limits any claimed embodiment and any claimed embodiments may cover processes or apparatuses that differ from those examples below described. The claimed embodiments are not limited to apparatuses or processes having all of the features of any one apparatus or process below described or to features common to multiple or all of the apparatuses or processes below described. Possible is that an apparatus or a process, below described, is not part of any claimed embodiment.

Furthermore, numerous specific details are set forth in order to provide a thorough understanding of the disclosure. However, understood is that the embodiments herein described may be practiced without these specific details. In other instances, well-known methods, procedures, and components have not been described in detail so as not to obscure the embodiments herein described.

As herein used, the terms, "comprises" and "comprising" are to be construed as being inclusive and open-ended, and not exclusive. Specifically, when used in the specification and claims, the terms, "comprises," and "comprising," and variations thereof, denote the specified features, steps, or components that are included. These terms are not to be interpreted to exclude the presence of other features, steps, or components.

As herein used, the terms "sample," "example," or "exemplary" denote "serving as an example, instance, or illustration," and should not be construed as preferred or advantageous over other configurations herein disclosed.

As herein used, the terms "about," "approximately," and "substantially" denote variations that may exist in the upper and lower limits of the ranges of values, such as variations in properties, parameters, and dimensions. In one non-limiting example, the terms "about," "approximately," and "substantially" are understood to denote plus or minus 10 percent or less.

Unless defined otherwise, all technical and scientific terms herein used are intended to have the same definition as commonly understood by one of ordinary skill in the art. Unless otherwise indicated, such as through context, as herein used, the following terms are intended to have the following definitions:

As herein used, the phrase "access port" refers to a cannula, conduit, sheath, port, tube, or other structure that is insertable into a subject in order to provide access to internal tissue, organs, or other biological substances. In some embodiments, an access port directly exposes internal tissue, for example, via an opening or aperture at a distal end thereof, and/or via an opening or aperture at an intermediate location along a length thereof. In other embodiments, an access port provides indirect access, via at least one surface that is transparent, or partially transparent, to one or more forms of energy or radiation, such as, but not limited to, electromagnetic waves and acoustic waves.

As herein used the phrase "intraoperative" refers to an action, process, method, event, or step that occurs, or is carried out, during at least a portion of a medical procedure. Intraoperative, as herein defined, is not limited to surgical procedures, and may refer to other types of medical procedures, such as diagnostic and therapeutic procedures.

Some embodiments of the present disclosure relate to minimally invasive medical procedures that are performed via an access port, whereby surgery, diagnostic imaging, therapy, or other medical procedures, e.g. minimally invasive medical procedures, are performed based on access to internal tissue through the access port. The present disclosure applies equally well to other medical procedures performed on other parts of the body, as well as to medical procedures that do not use an access port. Various examples of the present disclosure are generally suitable for use in any medical procedure that uses surgical microscopes, e.g., any medical procedure that may benefit from having intraoperative imaging at different magnification and/or focus settings.

In the example of a port-based surgery, a surgeon or robotic surgical system may perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue. A key to minimizing trauma is ensuring that the surgeon performing the procedure has the best possible view of the surgical site of interest without having to spend excessive amounts of time and concentration repositioning tools, scopes, and/or cameras during the medical procedure.

In various examples, the present disclosure describes an imaging system that addresses some of the above discussed challenges. For example, the disclosed imaging system enables a user, e.g., a surgeon, to obtain 3D views, high magnification narrow field views, and wide field views without having to switch between separate imaging systems. Further, the disclosed imaging system provides dual fieldsof-view (FOVs), in which narrow field and wide field views are simultaneously viewable. Using examples of the imaging system herein described, a surgeon may change between different viewing modes mid-surgery, such as switching to a 3D view when needed for depth perception, e.g., to perform complex vascular work, and switching to dual FOVs for situations where high magnification and situational context is desired, e.g., for suturing.

The systems and methods herein described are useful in the field of neurosurgery, including oncological care, neurodegenerative disease, stroke, brain trauma and orthopedic surgery. The teachings of the present disclosure are applicable to other conditions or fields of medicine. While the present disclosure describes examples in the context of neurosurgery, the present disclosure is applicable to other surgical procedures that use intraoperative optical imaging.

Various example apparatuses or processes are below described. No example embodiment below described limits any claimed embodiment and any claimed embodiments may cover processes or apparatuses that differ from those examples below described. The claimed embodiments are not limited to apparatuses or processes having all of the features of any one apparatus or process below described or to features common to multiple or all of the apparatuses or processes below described. Possible is that an apparatus or process below described is not part of any claimed embodiment.

Referring to FIG. 1, this diagram illustrates an access port 12 inserted into a brain 10, such as a human brain, the access port 12 providing access to internal tissue of the brain 10 during a medical procedure, in accordance with an embodiment of the present disclosure. The access port 12 has at least one lumen (not shown) that accommodates medical instruments, medical tools, or medical devices, such as catheters, surgical probes, and cylindrical ports, e.g., a NICO BrainPath™ device. Medical tools, such as surgical tools, and medical instruments are inserted within the at least one lumen of the access port 12 in order to perform medical procedures, such as surgical procedures, diagnostic procedures, and therapeutic procedures, e.g., resecting tumors, as desired or necessary. In the example of a port-based surgery, the access port 12 comprises a straight or linear configuration and is typically guided through a sulci path of the brain 10. Medical instruments are then inserted through the access port 12, e.g., via the at least one lumen.

Still referring to FIG. 1, the present disclosure applies equally well to catheters, deep brain stimulation (DBS) needles, a biopsy procedure, biopsies and/or catheters in other medical procedures performed on other parts of the body, and medical procedures that do not use an access port. Various examples of the present disclosure are generally suitable for use in any medical procedure that uses optical imaging systems.

Figure 2:
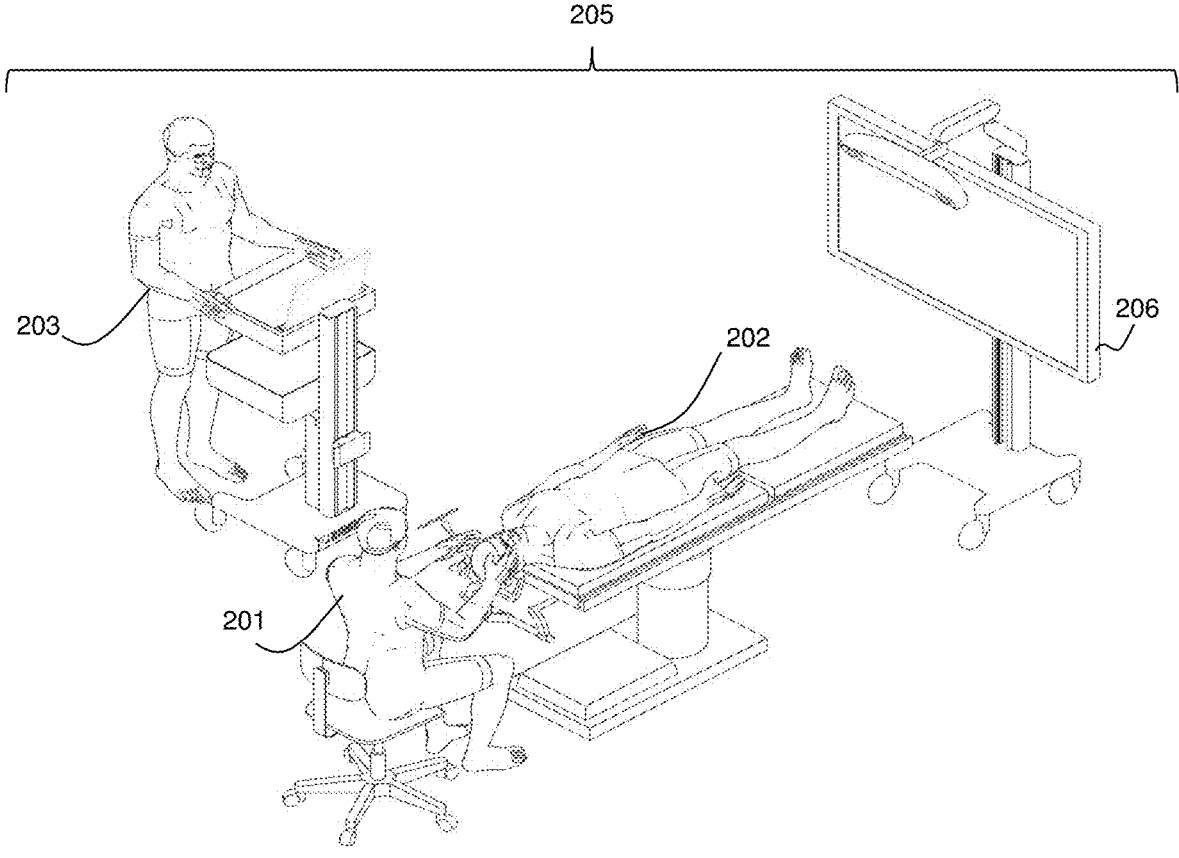
FIG. 2 is a diagram illustrating a navigation system configured to support image-guided surgery.

Referring to FIG. 2, this diagram illustrates a navigation system 205 configured to support image-guided surgery, in accordance with an embodiment of the present disclosure. A surgeon 201 conducts a surgery on a patient 202 in an operating room (OR) environment. A medical navigation system 205 comprises an equipment tower 207 (FIG. 3), a tracking system 321 (FIG. 4), displays 206, 211 (FIG. 3), and tracked instruments, e.g., medical instruments 360 (FIG. 4) to assist the surgeon 201 during a medical procedure. An operator 203 may also be present to operate, control, and provide assistance for the navigation system 205.

Figure 3:
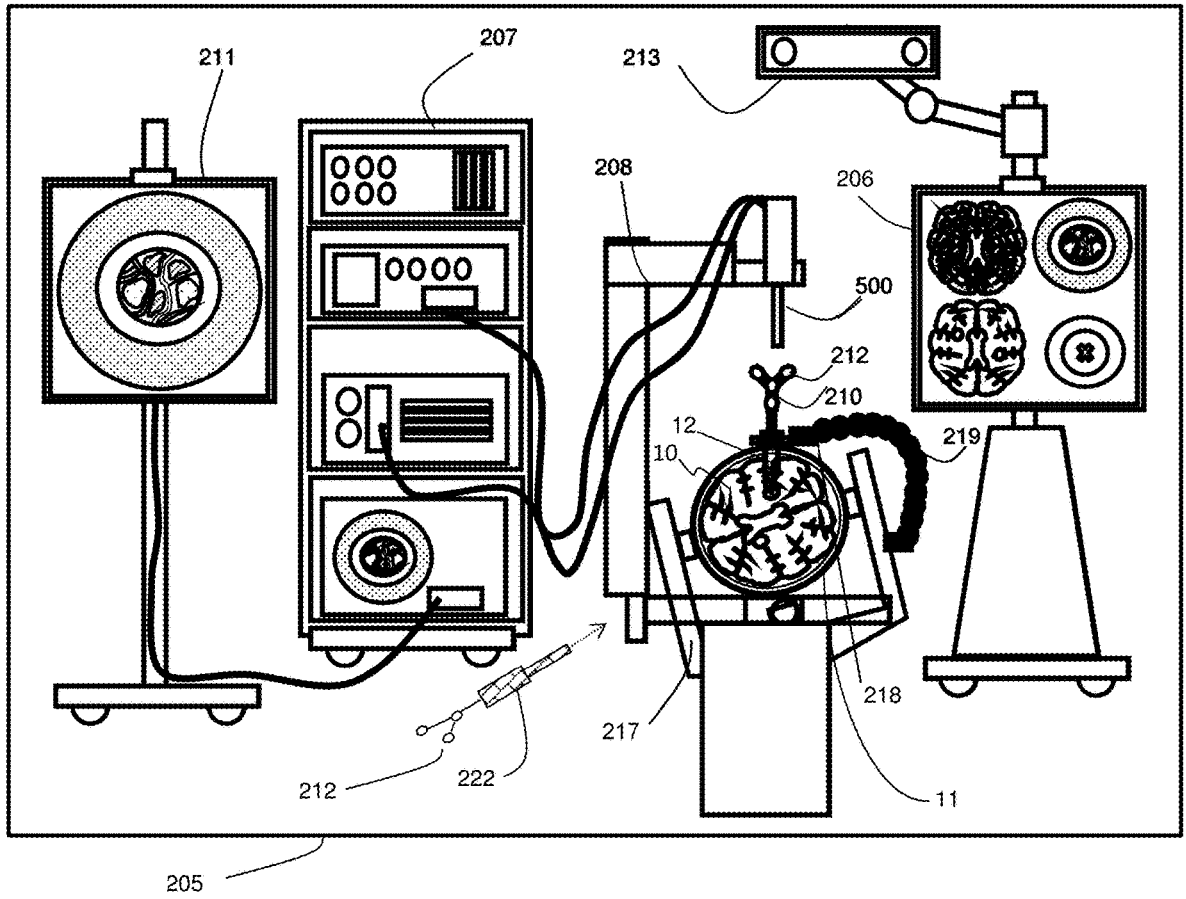
FIG. 3 is a diagram illustrating components of a navigation system configured to support image-guided surgery.

Referring to FIG. 3, this diagram illustrates components of a navigation system 205 configured to support image-guided surgery, in accordance with an embodiment of the present disclosure. An optical imaging system 500 is usable with the medical navigation system 205. The navigation system 205 comprises one or more displays 206, 211 for displaying a video image, an equipment tower 207, and a positioning system 208, e.g., comprising a mechanical arm, configured to support the optical imaging system 500. For example, the optical imaging system 500 comprises an optical scope (not shown). One or more of the displays 206, 211 comprises a touch-sensitive display for receiving touch input. The equipment tower 207 is coupled with a frame, e g., comprising at least one of a rack and a cart, and accommodates a power supply and a computer or controller configured to execute at least one of planning software, navigation software, and other software for managing at least one of the positioning system 208 and one or more medical instruments 360 being tracked by tracking system 321, e.g., of the navigation system 205. In some examples, the equipment tower 207 comprises a single tower configuration, operating with the displays 206, 211; however, the equipment tower 207 comprises other configurations as well, e.g., a dual tower configuration, a single display configuration, etc. Furthermore, the equipment tower 207 is further configured to accommodate a universal power supply (UPS) for providing emergency power in addition to an alternating current (AC) adapter power supply.

Still referring to FIG. 3, a portion of the patient's anatomy is retained by a holder. For example, the patient's head 11 and brain 10 are retained by a head holder 217. An access port 12 and associated introducer 210 is inserted into the head 11, to provide access to a surgical site in the head 11. The imaging system 500 is used to view down through the access port 12 at a sufficient magnification to allow for enhanced visibility down through the access port 12. The output of the imaging system 500 is received by one or more computers or controllers to generate a view displayable ion a video device, e.g., one or more displays 206, 211.

Still referring to FIG. 3, in some examples, the navigation system 205 comprises a tracked pointer 222. The tracked pointer 222, having markers 212 to enable tracking by a tracking camera 213, is used to identify points, e.g., fiducial points, on a patient. An operator 203, typically a nurse or the surgeon 201, uses the tracked pointer 222 to identify the location of points on the patient 202, in order to register the location of selected points on the patient 202 in the navigation system 205. Noted is that a guided robotic system with a closed loop control may be used as a proxy for human interaction. Guidance to the robotic system may be provided by any combination of input sources, such as image analysis, tracking of objects in the operating room using markers placed on various objects of interest, or any other suitable robotic system guidance techniques.

Still referring to FIG. 3, fiducial markers 212 are coupled with the introducer 210 for tracking by the tracking camera 213, which provide positional information of the introducer 210 from the navigation system 205. In some examples, the fiducial markers 212 are alternatively or additionally coupled with the access port 12. In some examples, the tracking camera 213 comprises a 3D infrared optical tracking stereo camera, such as a camera manufactured by Northern Digital Imaging (NDI). In some examples, the tracking camera 213 instead comprises an electromagnetic system (not shown), such as a field transmitter that uses one or more receiver coils located on the tool(s) to be tracked. A known profile of the electromagnetic field and a known position of the receiver coil(s) relative to each other is used to infer the location of the tracked tool(s) by using the induced signals and their phases in each of the receiver coils.

Operation and examples of this technology are further explained in Chapter 2 of "Image-Guided Interventions Technology and Application," Peters, T.; Cleary, K., 2008, ISBN: 978-0-387-72856-7, incorporated herein by reference. Location data of the positioning system 208 and/or the access port 12 are determined by the tracking camera 213 by detection of the fiducial markers 212 placed on or otherwise in fixed relation, e.g., in rigid connection, to any of the positioning system 208, the access port 12, the introducer 210, the tracked pointer 222, and/or other tracked instruments. The fiducial marker(s) 212 comprise active or passive markers. A display 206, 211 may provide an output of the computed data of the navigation system 205. In some examples, the output provided by the display 206, 211 comprises axial views, sagittal views, and coronal views of patient anatomy as part of a multi-view output.

Still referring to FIG. 3, the fiducial marker(s) 212, e.g., the active or passive fiducial markers, are coupled with the tools or the medical instruments 360, e.g., the access port 12 and/or the imaging system 500, to be tracked, to determine the location and orientation of these tools by using the tracking camera 213 and navigation system 205. The markers 212 are captured by a stereo camera of the tracking system 321 to give identifiable points for tracking the tools. A tracked tool is defined by a grouping of markers 212 which define a rigid body in relation to the tracking system 321. This definition, in turn, is used to determine the position and/or orientation in 3D of a tracked tool in a virtual space. The position and orientation of the tracked tool in 3D is tracked in six degrees of freedom, e.g., x, y, z coordinates and pitch, yaw, roll rotations, in five degrees of freedom, e.g., x, y, z, coordinate and two degrees of free rotation, but preferably tracked in at least three degrees of freedom, e.g., tracking the position of the tip of a tool in at least x, y, z coordinates. In typical use with navigation systems, at least three markers 212 are provided on a tracked tool to define the tool in virtual space; however, four or more markers 212 can be used.

Still referring to FIG. 3, camera images capturing the markers 212 are logged and tracked, by, for example, a closed circuit television (CCTV) camera. The markers 212 are selected to enable or assist in segmentation in the captured images. For example, infrared (IR)-reflecting markers and an IR light source from the direction of the camera are used. Examples of such apparatuses are tracking devices, such as a Polaris® system available from Northern Digital Inc. In some examples, the spatial position and the orientation of the tracked tool and/or the actual and desired position and orientation of the positioning system 208 are determined by optical detection using a camera. The optical detection is performed by using an optical camera, thereby rendering the markers 212 optically visible.

Still referring to FIG. 3, in some examples, the markers 212, e.g., reflectospheres, are used in combination with a suitable tracking system, to determine the spatial positioning position of the tracked tools within the operating theatre. Different tools and/or targets are provided with respect to sets of markers 212 in different configurations. Differentiation of the different tools and/or targets and their corresponding virtual volumes is possible based on the specification configuration and/or orientation of the different sets of markers 212 relative to one another, enabling each such tool and/or target to have a distinct individual identity within the navigation system 205. The individual identifiers provide information to the system, such as information relating to the size and/or shape of the tool within the system. The identifier also provides additional information, such as the tool's central point or the tool's central axis, among other information. The virtual tool is also determinable from a database of tools that is stored in, or provided to, the navigation system 205. The markers 212 are tracked relative to a reference point or reference object in the operating room, such as the patient 202.

Still referring to FIG. 3, various types of markers are used. The markers 212 comprise the same type or comprise a combination of two or more different types. Possible types of markers comprise reflective markers, radiofrequency (RF) markers, electromagnetic (EM) markers, pulsed or un-pulsed light-emitting diode (LED) markers, glass markers, reflective adhesives, or reflective unique structures or patterns, among others. RF and EM markers may have specific signatures for the specific tools to which they are coupled. Reflective adhesives, structures and patterns, glass markers, and LED markers are detectable using optical detectors, while RF and EM markers may be detectable using antennas. Different marker types may be selected to suit different operating conditions. For example, using EM and RF markers enables tracking of tools without requiring a line-of-sight from a tracking camera to the markers 212; and using an optical tracking system avoids additional noise from electrical emission and detection systems.

Still referring to FIG. 3, in some examples, the markers 212 comprise printed or 3D configurations that are used for detection by an auxiliary camera, such as a wide-field camera (not shown) and/or the imaging system 500. Printed markers may also be used as a calibration pattern, for example, to provide distance information, e.g., 3D distance information, to an optical detector. Printed identification markers comprise configurations, such as concentric circles with different ring spacing, and/or different types of barcodes, among other configurations. In some examples, in addition to, or in place of, using markers 212, the contours of known objects, e.g., the side of the access port 206, are captured and identified by using optical imaging devices and the tracking system 321.

Still referring to FIG. 3, a guide clamp 218 (or more generally a guide) for holding the access port 12 is provided. The guide clamp 218 allows the access port 12 to be held at a fixed position and a fixed orientation while freeing the surgeon's hands. An articulated arm 219 is provided to hold the guide clamp 218. The articulated arm 219 has up to six degrees of freedom to position the guide clamp 218. The articulated arm 219 is lockable to fix its position and its orientation, once a desired position is achieved. The articulated arm 219 is attached or attachable at a point, based on the patient head holder 217, or another suitable point, e.g., on another patient support, such as on the surgical bed, to ensure that, when locked in place, the guide clamp 218 does not move relative to the patient's head 11.

Still referring to FIG. 3, in a surgical operating room (or theatre), setup of a navigation system 205 may be relatively complicated as many pieces of equipment associated with the surgical procedure may also require setup in addition to elements of the navigation system 205 itself. Further, setup time typically increases as more equipment is added. To assist in addressing this, the navigation system 205 comprises two additional wide-field cameras to enable video overlay information. Video overlay information is inserted into displayed images, such as images displayed on one or more of the displays 206, 211. The overlay information displays the physical space where accuracy of the 3D tracking system (which is typically part of the navigation system) is greater, the available range of motion of the positioning system 208 and/or the imaging system 500, and/or facilitates guiding the head 11 and/or positioning the patient 202.

Still referring to FIG. 3, the navigation system 205 provides features to the neurosurgeon that may help to provide more relevant information to the surgeon and that may assist in improving performance and accuracy of port-based neurosurgical operations. Although described in the present disclosure in the context of port-based neurosurgery, e.g., for removal of brain tumors and/or for treatment of intracranial hemorrhages (ICH), the navigation system 205 is also suitable for one or more of: brain biopsy, functional/deep-brain stimulation, catheter/shunt placement (in the brain or elsewhere), open craniotomies, and/or endonasal/skull-based/ear-nose-throat (ENT) procedures, among others. The same navigation system 205 is used for performing any or all of these procedures, with or without modification, as appropriate.

Still referring to FIG. 3, for example, although the present disclosure describes the navigation system 205 in the context of neurosurgery, the navigation system 205 may be used to perform a diagnostic procedure, such as brain biopsy. A brain biopsy involves the insertion of a thin needle into a patient's brain 10 for purposes of removing a sample of brain tissue. The brain tissue is subsequently assessed by a pathologist to determine whether the brain tissue is cancerous, for example. Brain biopsy procedures are conducted with, or without, a stereotactic frame. Both types of procedures may be performed by using image-guidance. Frameless biopsies, in particular, may be conducted using the navigation system 205.

Still referring to FIG. 3, in some examples, the tracking camera 213 may be part of any suitable tracking system 321. In some examples, the tracking camera 213 (and any associated tracking system that uses the tracking camera 213) may be replaced with any suitable tracking system which may or may not use camera-based tracking techniques. For example, a tracking system that does not use the tracking camera 213, such as a radiofrequency tracking system, may be used with the navigation system 205.

Figure 4:
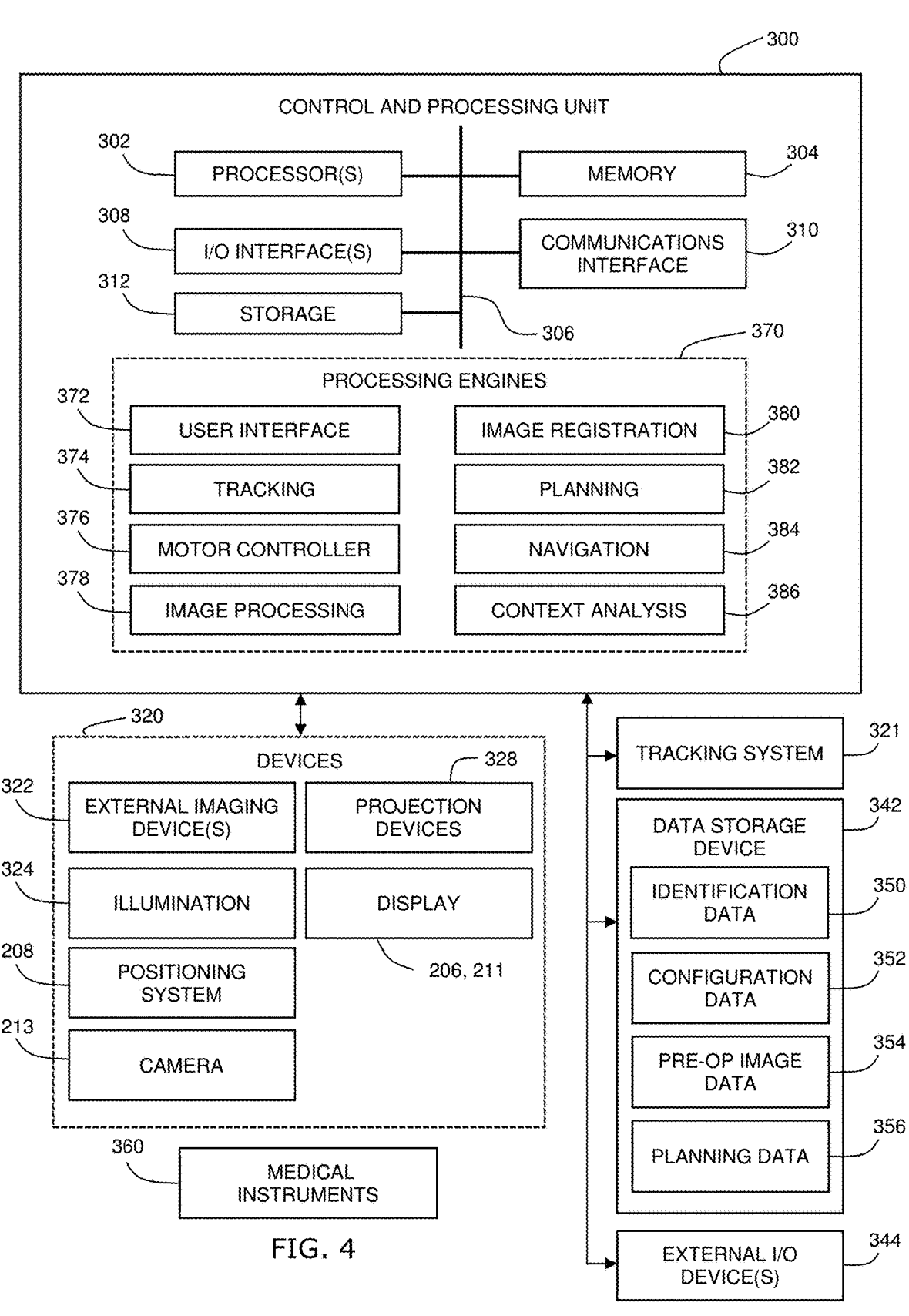
FIG. 4 is a block diagram illustrating a control and processing system usable with the navigation systems, as shown in FIGS. 2 and 3, a tracking system, at least one device, such as a positioning system, and at least one medical instrument.

Referring to FIG. 4, this block diagram illustrates the control and processing system 300 usable in the medical navigation system 205, as shown in FIG. 2, e.g., as part of the equipment tower 207, in accordance with an embodiment of the present disclosure. In one example, the control and processing system 300 comprises one or more processors 302, a memory 304, a system bus 306, one or more input/output interfaces 308, a communications interface 310, and a storage device 312. The control and processing system 300 interfaces with external devices, such as a tracking system 321, data storage 342, and external user input and output devices 344, such as one or more of a display, a keyboard, a mouse, sensors attached to medical equipment, a foot pedal, a microphone, and a speaker. Data storage 342 comprises any suitable data storage device, such as a local or remote computing device, e.g., a computer, hard drive, digital media device, or server, having a database stored thereon. In the example, the data storage device 342 stores identification data 350 for identifying one or more medical instruments 360 and configuration data 352 that associates customized configuration parameters with one or more medical instruments 360. The data storage device 342 may also store preoperative image data 354 and/or medical procedure planning data 356. Although the data storage device 342 is shown as a single device, in other embodiments, the data storage device 342 may be provided as multiple storage devices.

Still referring to FIG. 4, the medical instruments 360 are identifiable by the control and processing unit 300. The medical instruments 360 are coupled with, and controlled by, the control and processing unit 300, or the medical instruments 360 are operated, or otherwise employed, independent of the control and processing unit 300. The tracking system 321 is employed to track one or more medical instruments 360 and spatially register the one or more tracked medical instruments 360 to an intraoperative reference frame. For example, the medical instruments 360 have tracking markers 212, such as tracking spheres, that may be trackable using the tracking camera 213. In another example, a sheath placed over a medical instrument 360 has tracking markers 212.

Still referring to FIG. 4, the control and processing unit 300 interfaces with a number of devices 320. The devices 320 comprise configurable devices, which are preoperatively and/or intraoperatively reconfigured by the control and processing unit 300, e.g., based on configuration parameters obtained from the configuration data 352. Examples of devices 320 include the surgical microscope system 500, one or more illumination devices 324, the positioning system 208, the tracking camera 213, one or more projection devices 328, and one or more displays 206, 211.

Still referring to FIG. 4, some or all functionalities herein described may be implemented using the control and processing unit 300. For example, the memory 304 may store instruments, as one or more processing modules or engines 370, executable by the processor(s) 302. Example processing modules include, but are not limited to, a user interface engine 372, a tracking module 374, a motor controller 376, an image processing engine 378, an image registration engine 380, a procedure planning engine 382, a navigation engine 384, and a context analysis module 386. While example processing engines 370 are shown, instructions may be stored in the memory 304 in any suitable form. In some examples, two or more of the processing engines 370 may be used together to perform a function. Although depicted as separate processing engines 370, the processing engines 370 may be embodied as a unified set of computer-readable instructions, e.g., stored in the memory 304 rather than distinct sets of instructions. In some examples, software instructions stored in the memory 304 may be used together with hardware logic implemented by the processor(s) 302. In some examples, functionalities herein disclosed may be implemented by the control and processing unit 300 in cooperation with another controller, such as a controller of the surgical microscope system 500, described further below.

Still referring to FIG. 4, understood is that the system is not intended to be limited to the components shown. One or more components of the control and processing system 300 may be provided as an external component or device. In one example, the navigation module 384 may be provided as an external navigation system that is integrated with the control and processing system 300. Some embodiments may be implemented, using the processor 302, without additional instructions stored in memory 304. Some embodiments may be implemented using the instructions stored in memory 304 for execution by one or more general purpose microprocessors. Thus, the present disclosure is not limited to a specific configuration of hardware and/or software.

Still referring to FIG. 4, in some examples, the navigation system 205, which may include the control and processing unit 300, may provide tools to the surgeon that may help to improve the performance of the medical procedure and/or post-operative outcomes. In addition to removal of brain tumours and intracranial hemorrhages (ICH), the navigation system 205 is also applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, examples of the present disclosure may be applied to any suitable medical procedure.

Figure 5:
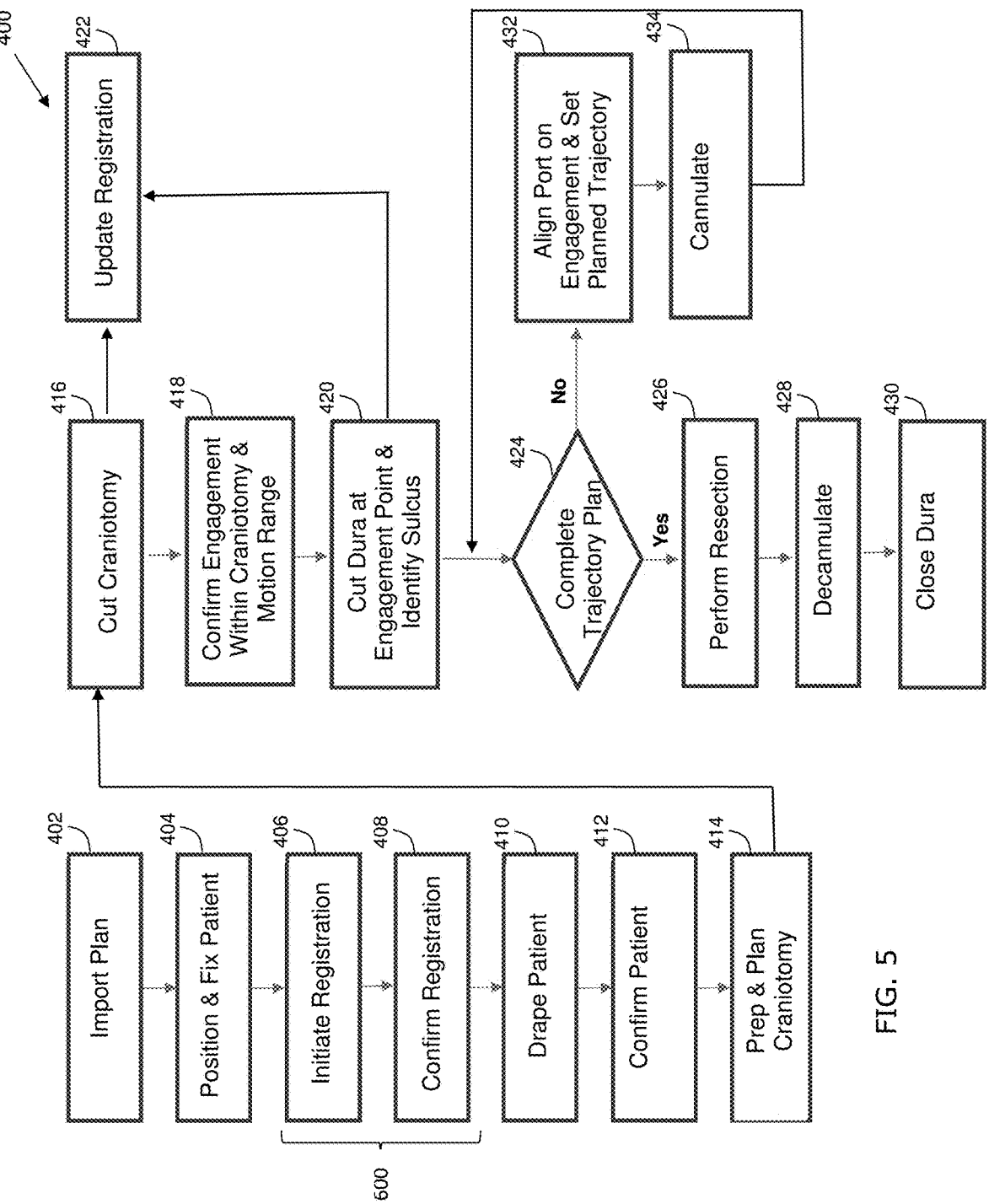
FIG. 5 is a flow diagram illustrating a method of performing a medical procedure, such as a surgical procedure, by way of a navigation system, such as the navigation systems, as shown in FIGS. 2 and 3, configured to support image-guided surgery.

Referring to FIG. 5, this flow diagram illustrates a method 400 of performing a medical procedure, such as a surgical procedure, implementable by using a navigation system, such as the navigation systems 205, as shown in FIGS. 2 and 3, configured to support image-guided surgery, in accordance with an embodiment of the present disclosure. At a first step 402, the port-based surgical plan is imported. Once the plan is imported into the navigation system at step 402, the patient 202 is affixed into position using a body holding mechanism. The head position is also confirmed with the patient plan in the navigation system at step 404, which, in one example, is implemented by the computer or controller as part of the equipment tower 207. Next, registration of the patient is initiated at step 406. The phrase "registration" or "image registration" refers to the process of transforming different sets of data into one coordinate system. Data comprises multiple photographs, data from different sensors, times, depths, or viewpoints. The process of "registration" is used in the present application for medical imaging in which images from different imaging modalities are co-registered. Registration is used in order to be able to compare or integrate the data obtained from these different modalities.

Still referring to FIG. 5, numerous registration techniques are available and one or more of the techniques may be applied to the present example and are also encompassed by the present disclosure. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images are co-registered, while multi-modality registration methods are used to register images acquired by different scanner or sensor types, for example in magnetic resonance imaging (MRI) and positron emission tomography (PET). In the present disclosure, multi-modality registration methods are used in medical imaging of the head 11 and/or brain 10 as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT.

Figure 6:
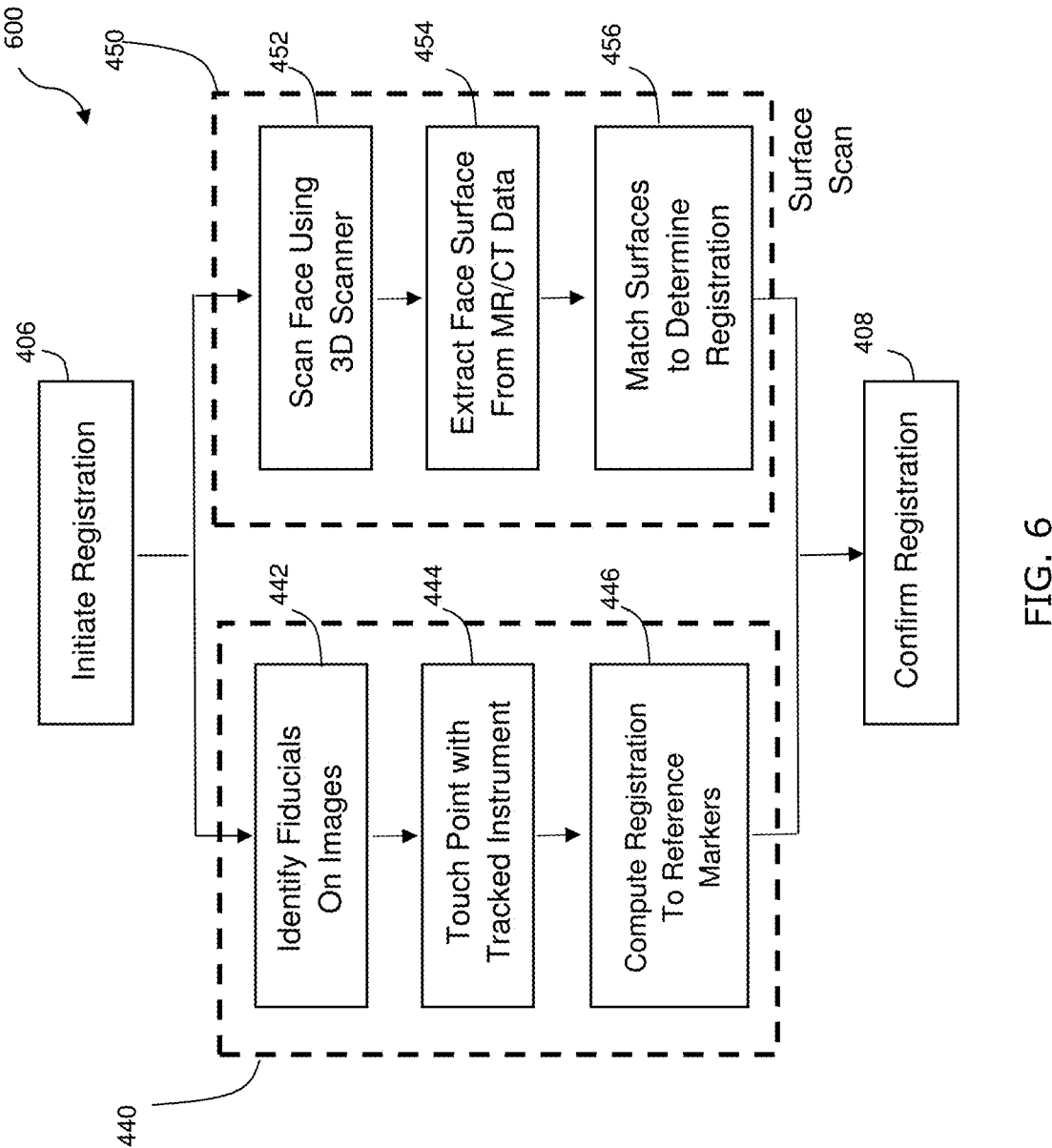
FIG. 6 is a flow diagram illustrating a method of registering a patient for a medical procedure, such as a surgical procedure, as shown in FIG. 5, by way of a navigation system, such as the navigation systems, as shown in FIGS. 2 and 3, configured to support image-guided surgery.

Referring to FIG. 6, this flow diagram illustrates a method 600 of registering a patient 202 for a medical procedure, such as a surgical procedure, as shown in FIG. 5, implementable by using a navigation system, such as the navigation systems 205, as shown in FIGS. 2 and 3, configured to support image-guided surgery, in accordance with an embodiment of the present disclosure. If fiducial touch points are used, the method 600 comprises performing a step 440, the step 440 comprising: identifying fiducials on images at substep 442, touching the touch points with a tracked instrument at substep 444, and, using, the control and processing system 300 of the navigation system 205, computing the registration to reference markers at substep 446. Alternatively, if fiducial touch points are not being used, the method 600 comprises performing a surface scan at step 450, the step 450 comprising: scanning the face by using a 3D scanner at substep 452, extracting the face surface from MR/CT data at substep 454, and matching surfaces to determine registration data points at substep 456. Upon completion of either step 440 or step 450, performing step 408 comprises: extracting registration data points, computing the registration, and confirming the registration.

Referring back to FIG. 5, once registration is confirmed at step 408, the patient 202 is draped at step 410. Typically, draping involves covering the patient 202 and surrounding areas with a sterile barrier to create and maintain a sterile field during the surgical procedure. The purpose of draping is to eliminate the passage of microorganisms, e.g., bacteria, between non-sterile and sterile areas. At this point, conventional navigation systems require that the non-sterile patient reference is replaced with a sterile patient reference of identical geometry location and orientation.

Still referring back to FIG. 5, upon completion of draping at step 410, the patient engagement points are confirmed at step 412 and the craniotomy is prepared and planned at step 414. Upon completion of the preparation and planning of the craniotomy at step 414, the craniotomy is cut and a bone flap is temporarily removed from the skull to access the brain 10 at step 416. Registration data is updated with the navigation system at this point at step 422. Next, the engagement within craniotomy and the motion range are confirmed at step 418. Next, the procedure advances to cutting the dura at the engagement points and identifying the sulcus at step 420.

Still referring back to FIG. 5, thereafter, the cannulation process is initiated at step 424. Cannulation involves inserting an access port 12 into the brain 10, typically along a sulci path as identified at 420, along a trajectory plan. Cannulation is typically an iterative process that involves repeating the steps of aligning the access port 12 on engagement and setting the planned trajectory at step 432 and then cannulating to the target depth at step 434 until the complete trajectory plan is executed at step 424.

Still referring back to FIG. 5, once cannulation is complete, the surgeon 201 then performs resection at step 426 to remove part of the brain 10 and/or tumor of interest. The surgeon 201 then decannulates at step 428 by removing the access port 12 and any tracking instruments from the brain 10. Finally, the surgeon 201 closes the dura and completes the craniotomy at step 430. Some aspects of the method 400 are specific to port-based surgery, such as portions of steps 428, 420, and 434, but the appropriate portions of these steps may be skipped or suitably modified when performing non-port based surgery.

Referring back to FIGS. 5 and 6, when performing a surgical procedure using a navigation system 205, the navigation system 205 acquires and maintains a reference of the location of the tools in use as well as the patient in three-dimensional (3D) space. In other words, during a navigated neurosurgery, a tracked reference frame is fixed, e.g., relative to the patient's skull. During the registration phase of a navigated neurosurgery, e.g., the step 406, a transformation is calculated that maps the frame of reference of preoperative MRI or CT imagery to the physical space of the surgery, specifically the patient's head 11. This may be accomplished by the navigation system 205 tracking locations of fiducial markers 212 fixed to the patient's head 11, relative to the static patient reference frame. The patient reference frame is typically rigidly attached to the head fixation device, such as a Mayfield clamp. Registration is typically performed before the sterile field has been established, e.g., the step 410.

Figure 7:
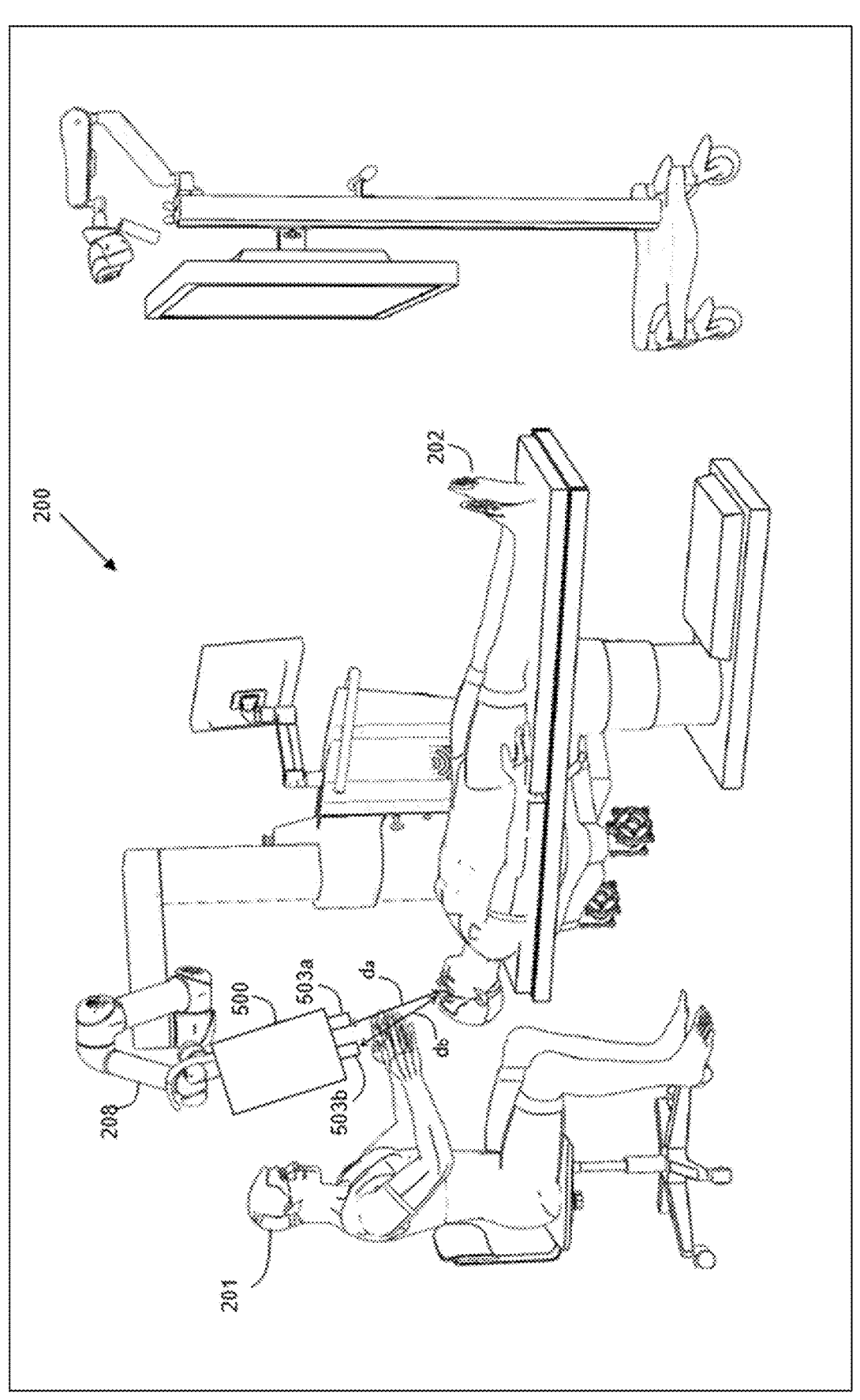
FIG. 7 is a diagram illustrating an optical imaging system, comprising a medical microscope, and a positioning system usable during a medical procedure, such as a surgical procedure, as shown in FIG. 5.

Referring to FIG. 7, this diagram illustrates an optical imaging system 500, comprising a medical microscope, and a positioning system, such as the positioning system 208, usable during a medical procedure, such as a surgical procedure, as shown in FIG. 5, in accordance with an embodiment of the present disclosure. Although the imaging system 500 is shown as being used in a navigation system environment 200, e.g., using a navigation system as above described, the imaging system 500 may also be used outside of a navigation system environment, e.g., without any navigation support.

Still referring to FIG. 7, an operator, typically a surgeon 201, may use the imaging system 500 to observe the surgical site, e.g., to look down through an access port 12. The imaging system 500 is coupled with the positioning system 208, e.g., a controllable and adjustable robotic arm. The position and the orientation of at least one of the positioning system 208, the imaging system 500, and the access port 12 are tracked by using a tracking system, such as the tracking system 321 of the navigation system 205. The imaging system 500 comprises two apertures 503a, 503b, e.g., one aperture for each optical assembly. The respective apertures 503a, 503b of the optical assemblies are independently adjustable, thereby enabling each optical assembly to have independently controllable resolution and independently controllable depth-of-field. The respective distances $d_a$, $d_b$ between the apertures 503a, 503b and the viewing target, e.g., the surface of the surgical site, are referred as the respective working distance of each optical assembly. The imaging system 500 is configured for use in a predefined range of working distance, e.g., in the range of approximately 20 cm to approximately 65 cm). The imaging system 500 is coupled with the positioning system 208; and the actual available range of working distance may depend on both the working distance of the imaging system 500 as well as the workspace and kinematics of the positioning system 208.

Figure 8:
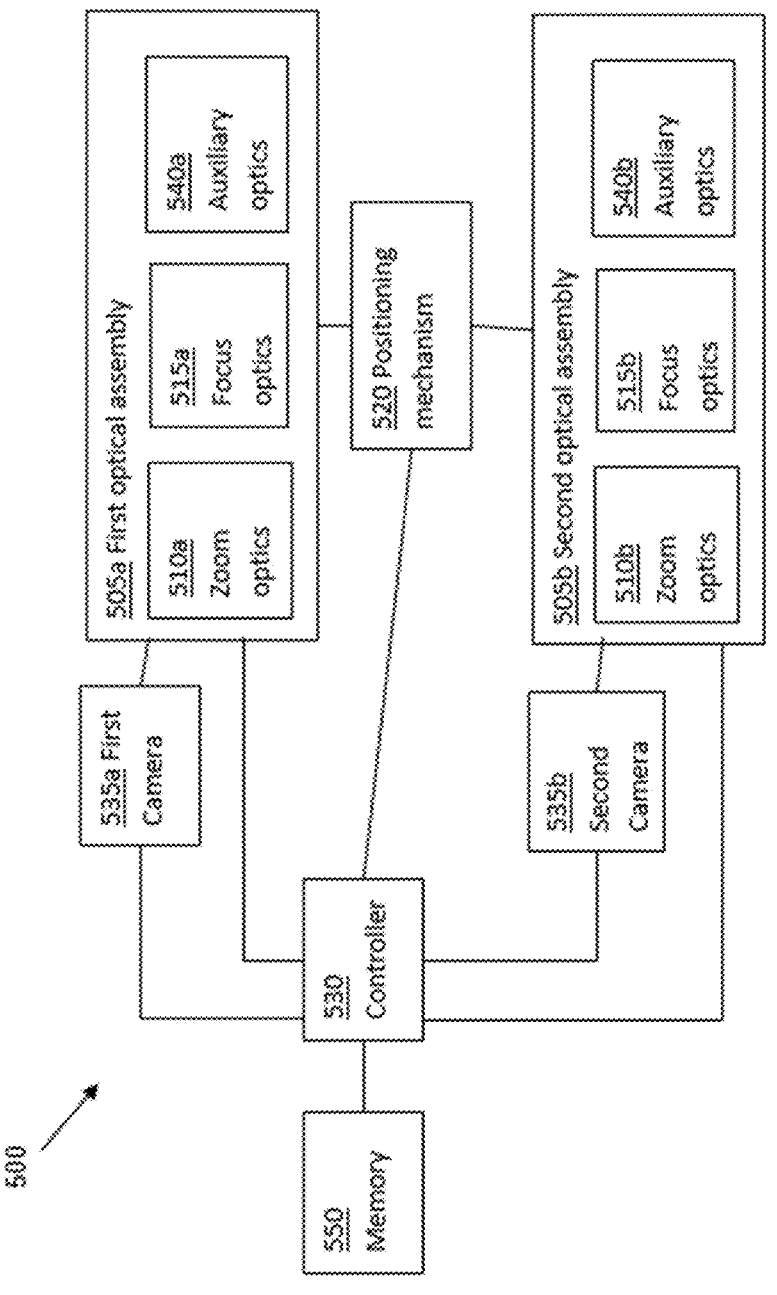
FIG. 8 is a block diagram illustrating components of an optical imaging system.

Referring to FIG. 8, this block diagram illustrates components of an optical imaging system, e.g., the imaging system 500, in accordance with an embodiment of the present disclosure. The imaging system 500 comprises first and second optical assemblies 505a, 505b (also referred as optical trains), each of which is independently operable or cooperatively operable. Each optical assembly 505a, 505b captures an image received through the respective apertures 503a, 503b.

Still referring to FIG. 8, for simplicity, the first optical assembly 505a is described in detail; and the second optical assembly 505b may have the same components and function as those of the first optical assembly 505a, for example, as below described. The first optical assembly 505a comprises optics, e.g., lenses, optical fibers, etc., for focusing and zooming on the viewing target. The first optical assembly 505a comprises zoom optics 510a (which may include one or more zoom lenses) and focus optics 515a (which may include one or more focus lenses). Each of the zoom optics 510a and focus optics 515a are independently moveable within the optical assembly, in order to adjust the zoom and focus, respectively. Where the zoom optics 510a and/or the focus optics 515a include more than one lens, each individual lens is independently moveable. The aperture 503a of the first optical assembly 505a is adjustable. The first optical assembly 505a comprises one or more auxiliary optics 540a, e.g., rotational optics and/or aperture adjustment), which may be static or dynamic. For example, the auxiliary optics 540a comprise rotational optics, e.g., prisms, to enable the user to define the orientation of the captured image. The rotational optics of each optical assembly 505a, 505b are independently adjustable, thereby enabling each optical assembly 505a, 505b to capture independently rotation images. Alternatively, instead of using rotation optics, software image processing is performed to rotate a captured image to the desired orientation. Each optical assembly 505a, 505b also comprises one or more filters, each filter being independently configurable, e.g., for different wavelengths, polarizations, neutral densities, or other characteristics. The filters are disposed in the optical path, e.g., using filter wheels or other similar mechanisms. Each optical assembly 505a, 505b may have different filters.

Still referring to FIG. 8, the imaging system 500 comprises one or more positioning mechanisms 520, e.g., gear train, rack and gear system, conveyor mechanism or linear stage mechanism, for positioning the first and second optical assemblies 505a, 505b relative to each other. For simplicity, the present disclosure may refer to the positioning mechanism 520 in the singular; however, the present disclosure also includes embodiments, wherein the positioning mechanism 520 includes a plurality of such mechanisms.

Still referring to FIG. 8, in some examples, the imaging system 500 comprises a light source or the imaging system 500 directs light from an external light source for illuminating the viewing target. The light source (whether internal or external to the imaging system 500) is capable of providing different wavelengths of light and different bandwidths, for example, including broadband illumination for white light imaging or narrow band illumination in the fluorescence spectrum for fluorescence imaging. Fluorescence imaging involves the use of appropriate excitation and emission filters. The wavelength characteristics of the filter are typically specific to the fluorophore used.

Figure 9:
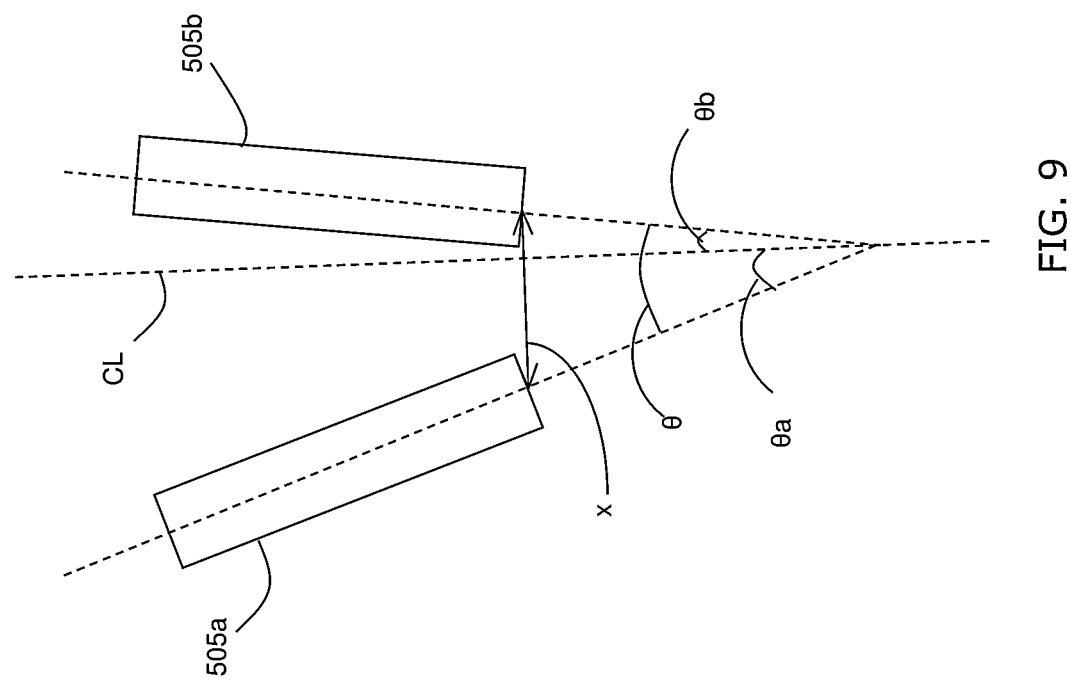
FIG. 9 is a diagram illustrating a relative position and a relative orientation of optical assemblies of an optical imaging system, as shown in FIG. 8.

Referring to FIG. 9, this diagram illustrates a relative position and a relative orientation of optical assemblies of an optical imaging system, as shown in FIG. 8, in accordance with an embodiment of the present disclosure. The positions and orientations of the optical assemblies 505a, 505b are described with reference to the optical axes of each optical assembly 505a, 505b. Generally, the optical axis of an optical assembly 505a, 505b is defined as the axis along which light travels from the viewing target to the aperture of the optical assembly 505a, 505b, and is the longitudinal axis of the optical assembly 505a, 505b. The working distance of the optical assembly 505a, 505b is typically also measured along the optical axis. The positioning mechanism 520 is used to control the lateral separation x between the optical axes of the optical assemblies 505a, 505b, and the angle θ between the optical axes of the optical assemblies 505a, 505b. Where the optical axes are not parallel to each other, lateral separation between the optical axes is measured as the lateral distance between the apertures of the optical assemblies 505a, 505b. The angle θ between the optical axes is alternatively defined as the summation of respective angles $\theta_a$, $\theta_b$ of each optical axis relative to a common centerline CL of the imaging system 500. In some examples, the positioning mechanism 520 comprises separate mechanisms for controlling position and orientation of each optical assembly 505a, 505b. In some examples, the same positioning mechanism 520 is used to control the position and the orientation of both optical assemblies 505a, 505b. The lateral separation and angle may be separately and independently controlled, and may be controlled using separate positioning mechanisms 520 for lateral separation and for angular orientation.

Still referring to FIG. 9 and referring back to FIG. 8, operation of the optics in the first and second optical assemblies 505a, 505b may be controlled by a controller 530, e.g., a microprocessor, of the imaging system 500. The controller 530 receives control input, e.g., from an external system, such as an external processor or an input device. The control input directs the controller 530 to control the optical assemblies 505a, 505b in one of various possible modes of operation, as below further discussed. The controller 530 directly controls movement of at least one of the zoom optics 510a, 510b and the focus optics 515a, 515b. Alternatively, the controller 530 provides instructions to a respective sub-controller (not shown) of each optical assembly 505a, 505b to control at least one of the respective zoom optics 510a, 510b and the focus optics 515a, 515b.

Still referring to FIG. 9 and referring back to FIG. 8, the controller 530 also controls the positioning mechanism 520 to control the relative position and the relative orientation of the optical assemblies 505a, 505b. For example, the controller 530 controls the positioning mechanism 520 to position/orient at least one of: only one of the optical assemblies 505a, 505b, each optical assembly 505a, 505b independently of the other, both optical assemblies 505a, 505b simultaneously, and both optical assemblies 505a, 505b cooperatively, as below further discussed.

Still referring to FIG. 9 and referring back to FIG. 8, the imaging system 500 further comprises first and second cameras 535a, 535b, e.g., high-definition (HD) cameras, for each respective optical assembly 505a, 505b to capture image data from the respective optical assembly 505a, 505b. Operation of the cameras 535a, 535b is controlled by the controller 530. The cameras 535a, 535b also output data to an external system, e.g., an external workstation or external output device, to view the captured image data. In some examples, the cameras 535a, 535b output data to the controller 530, which in turn transmits the data to an external system for viewing. By providing image data to an external system for viewing, the captured images are viewed on a larger display and are displayed together with other information relevant to the medical procedure, e.g., a wide-field view of the surgical site, navigation markers, 3D images, etc.

Still referring to FIG. 9 and referring back to FIG. 8, the controller 530 is coupled with a memory 550. The memory 550 is internal or external in relation to the imaging system 500. Data received by the controller 530, e.g., image data from the cameras 535a, 535b, is stored in the memory 550. The memory 550 stores instructions configuring the controller to operate the positioning mechanism 520 and/or to control the zoom and focus of each optical assembly 505a, 505b. For example, the memory 550 stores instructions to enable the controller to control the optical assemblies 505a, 505b independently or cooperatively, as below further discussed.

Still referring to FIG. 9 and referring back to FIG. 8, the imaging system 500 communicates with an external system, e.g., a navigation system or a workstation, via wired or wireless communication. In some examples, the imaging system 500 comprises a wireless transceiver (not shown) to enable wireless communication. An external processor, e.g., a processor of a workstation or the navigation system, in communication with the controller 530 is used to provide control input to the controller 530. For example, the external processor provides a graphical user interface via which the operator or an assistant enters instructions to control operation of the imaging system 500. The controller 530 is alternatively, or additionally, in communication with an external input system, e.g., a voice recognition input system or a foot pedal.

Still referring to FIG. 9 and referring back to FIG. 8, the imaging system 500 comprises a power source, e.g., a battery, or a connector to a power source, e.g., an AC adaptor. In some examples, the imaging system 500 receives power via a connection to an external system, e.g., an external workstation or processor. In some examples, the first and second optical assemblies 505a, 505b are housed in a common housing (not shown). The housing is sized to allow relative movement between the optical assemblies 505a, 505b within preset boundaries. In some examples, other components of the imaging system 500 are housed in the same housing.

Still referring to FIG. 9 and referring back to FIG. 8, the imaging system 500 is configured to couple with a moveable support structure, such as the positioning system, e.g., robotic arm, of a navigation system, a manually operated support arm, a ceiling mounted support, a moveable frame, or other such support structure. The imaging system 500 is removably coupled with the moveable support structure. In some examples, the imaging system 500 comprises a support connector, e.g., a mechanical coupling, to enable the imaging system 500 to be quickly and easily mounted or dismounted from the support structure. The support connector on the imaging system 500 is configured to couple with a complementary connector of the support structure, e.g., configured to couple with a variety of end effectors. In some examples, the imaging system 500 is coupled with the support structure together with other end effectors. Alternatively, the imaging system 500 is coupled with the support structure via another end effector.

Still referring to FIG. 9 and referring back to FIG. 8, when mounted, the imaging system 500 is disposed at a known fixed position and a known fixed position orientation relative to the support structure, e.g., by calibrating the position and the orientation of the imaging system 500 after mounting. In this way, by determining the position and the orientation of the support structure, e.g., using a navigation system or by tracking the movement of the support structure from a known starting point, the position and the orientation of the imaging system 500 may also be determined. In some examples, the imaging system 500 comprises a manual release button that, when actuated, enables the imaging system 500 to be manually positioned, e.g., without software control by the support structure.

As above discussed, the two optical assemblies of the imaging system may be controlled independently or cooperatively. The magnification and focus of each optical assembly may similarly be controlled independently or cooperatively between the optical assemblies. The imaging system may operate in one of several modes: for example including independent mode, dual-FOV mode, stereoscopic mode, and depth map mode. The imaging system may receive control input from an external system or from an input mechanism to select the mode of operation and to switch between different modes of operation. The surgeon or other operator may control the imaging system to switch between different modes of operation intraoperatively.

In the independent mode, the controller may control each optical assembly independently, such that the two optical assemblies may function similarly to two separate microscopes and may capture images of different target objects. The controller may control the zoom and focus optics of each optical assembly independently, in response to control input. Each optical assembly may also be positioned and oriented independently of each other (within the constraint that the optical assemblies should not collide with each other), in order to capture different FOVs, for example. The cameras associated with each optical assembly may also operate independently. Image data from each optical assembly may be communicated separately and may be displayed separately. For example, the first optical assembly and first camera may capture images of a first target, and this image data may be communicated to a desktop computer for display on a desktop display; the second optical assembly and second camera may capture images of a second target, and this image data may be communicated to a projection device for display on a projection screen. In some examples, the captured images may be displayed side-by-side on the same display device. The controller of the imaging system may manage and route the image data accordingly, in response to the operator's control input.

In the dual-FOV mode, the optical assemblies may be controlled to view the same target object. However, the zoom optics of each optical assembly may be controlled separately such that the first optical assembly provides a FOV that is different from the FOV of the second optical assembly. Each optical assembly may thus provide a respective two-dimensional (2D) view of the target object, but with different FOVs. For example, the first optical assembly may provide a larger FOV than the second optical assembly, and the FOV provided by the second optical assembly may fall entirely within the FOV of the first optical assembly. The FOV of each optical assembly may be controlled independently, in response to control input. The surgeon may control the imaging system to focus on a certain target object and may select the zoom or FOV size for each optical assembly. As the imaging system is controlled to view different viewing targets, each optical assembly may change its focus accordingly, while maintaining the respective selected zoom. In some examples, the zoom or FOV size for each optical assembly may be selected by specifying a relative difference between the zooms or FOV sizes, e.g., presetting that one FOV should be twice the magnification of the other FOV); and/or may be selected by specifying the zoom or FOV size explicitly, e.g., in percentage magnification. Since the FOV of each optical assembly may be controlled independently, one FOV may be fixed while the other is varied, the two FOVs may be the same, and the optical assemblies may switch between having larger or smaller FOVs between the two, for example. The use of the dual-FOV mode may provide the surgeon with a magnified view of the surgical target while simultaneously providing the surgeon with a wider contextual view of the surgical field. Similar to the independent mode, the image data captured by the first and second cameras may be displayed separately or side-by-side, for example.

In some examples, 3D images may be obtained using the dual-FOV mode. For example, where the FOV of the first optical assembly overlaps with or entirely includes the FOV of the second optical assembly, both sets of image data may be communicated to an external system, e.g., an image viewing workstation. The external system may determine the image portion that is common between the two FOVs and may generate a 3D image, e.g., using appropriate 3D image rendering techniques, using the two sets of image data, for this common image portion.

In the stereoscopic mode, the optical assemblies may be controlled to view the same target object using the same FOV. Because of the separation of the optical assemblies, the result is that the two optical assemblies may cooperate together to function similarly to a stereoscopic microscope, with the cameras of each optical assembly being used to capture a respective one of a pair of stereo images. The surgeon may control the imaging system to focus on a certain target object at a certain FOV. As the imaging system is controlled to view different viewing targets, each optical assembly may change its focus accordingly so that they continue to focus on a common viewing target. The surgeon may control the imaging system to change the zoom or FOV, and each optical assembly may adjust its zoom accordingly. The image data captured by the first and second cameras may be communicated to an external system, e.g., an image viewing workstation, that may use the two sets of data to generate a 3D image, e.g., using appropriate 3D rendering techniques. The 3D image may be presented as a rendered 3D model on a conventional 2D display, and/or may be viewed as a 3D image using 3D viewing technology, e.g., requiring the use of 3D glasses. The 3D image may be provided as part of an augmented reality display, for example. In some examples, the imaging system in the stereoscopic mode may operate similarly to the dual-FOV mode, with the difference that the two optical assemblies share the same FOV.

In some examples, the image data captured using the disclosed imaging system may be used for an augmented reality display. Using augmented reality, video information captured by the imaging system may be displayed together with images from other imaging modalities, e.g., intra-operative imaging modalities such as optical coherence tomography (OCT), ultrasound, fluorescence imaging and elastography, or pre-operative imaging modalities, such as MRI, CT, PET, functional MRI (fMRI), and diffusion tensor imaging (DTI). The image information captured from both optical assemblies may be at the same level of magnification to provide a 3D stereoscopic view of the target, e.g., as above described, or at different levels of magnification to provide different FOVs, for example. When different FOVs are provided, using augmented reality to superimpose anatomical structures on the narrower FOV may help the surgeon to reduce or avoid the risk of damaging brain cells while a wider FOV overlay may provide information to help enhance the surgeon's understanding of the spatial relationship between different structures and their functional status.

Noted is that, unlike conventional stereoscopic microscopes, the disclosed imaging system allows for the lateral separation of the optical assemblies to be adjusted. Since there is a relationship between lateral stereo separation and working distance, the ability of the disclosed imaging system to dynamically adjust lateral separation may provide for a more comfortable viewing experience, e.g., enabling more comfortable viewing of 3D images, with less eye strain and/or headaches), for example by more accurately mimicking the natural separation between the viewer's eyes.

In the depth map mode, each optical assembly may be used to view a different depth of field, while focused on the same target object and in the same FOV. For example, the first optical assembly may provide a greater depth of field, e.g., 1 cm, than the second optical assembly, e.g., 1 mm. The second optical assembly may be controlled to automatically move through the depth range of the first optical assembly to capture images at different depths, e.g., at increments of 1 mm, through the depth range. The image data captured by the second optical assembly at different depths may be transmitted, together with the image data captured by the first optical assembly, to an external system, e.g., an image viewing workstation. The image data from the second optical assembly at different depths may be aggregated into a set of depth images to form a depth map for the same FOV as the image data from the first optical assembly. The depth map may provide focused views of the FOV, at different depths, and may include contours, color-coding and/or other indicators of different depths. Image processing may be performed to generate a pseudo 3D image, for example by visually encoding, e.g., using color, artificial blurring or other visual symbols, different parts of the captured image according to the depth information. The external system may provide a user interface that allows a user to navigate through the depth map, for example.

In some examples, a depth map may be generated by comparing image information from two different vantage points coming from the two optical assemblies. The apparent pixel difference between these two images, also referred to as a disparity map, may be used to generate a depth map. Examples of the present disclosure may enable different viewing modes, e.g., stereoscopic mode and dual-FOV mode, to be implemented using a single imaging system, without having to switch between different imaging systems. An operator may conveniently switch between the different modes depending on the desired imaging. Although the above examples describe the use of an external system such as an image viewing workstation for processing image data from the imaging system, in some examples some or all of the image processing may be performed by the controller of the imaging system itself.

Generally, when operating in the independent mode, the controller of the imaging system may control the optical assemblies in an uncoupled configuration, where each optical assembly is controlled entirely independently of the other. When in the uncoupled configuration, the positioning mechanism may mechanically uncouple the optical assemblies from each other. In some examples where there are separate positioning mechanisms for each optical assembly, the positioning mechanisms may simply operate independently.

When operating in the dual-FOV mode, the stereoscopic mode or the depth map mode, the controller may control the optical assemblies in a coupled configuration, where the focus and/or zoom of one optical assembly is dependent on that of the other, and where the position and/or orientation of one optical assembly is dependent on that of the other. For example, the optical axes and/or focus optics of each optical assembly may be adjusted so that a common focus is maintained even as the viewing target is moved, or as the working distance is adjusted. When in the coupled configuration, the positioning mechanism may serve to mechanically couple the optical assemblies to each other.

In some examples, the disclosed imaging system may be used with a navigation system, e.g., as described above. The navigation system may provide tracking of a viewing target, e.g., by tracking a pointer tool or other medical instrument, and the controller may control the imaging system to automatically adjust focus to follow the tracked target. The navigation system may also provide information to help with positioning of the imaging system relative to the tracked target, e.g., using a robotic positioning system. Although the above discussion refers to the surgeon as being the user who controls and uses the examples of the present disclosure, the present disclosure is not limited to any specific user. In some examples, there may be a plurality of users involved.

Referring back to FIG. 7, this diagram illustrates an exemplary navigation system environment 200, which may be used to support an image-guided medical procedure. A surgeon 201 conducts a surgery on a patient 202 in an operating room (OR) environment. A medical navigation system 205 comprises an equipment tower, tracking system, display(s) and tracked instrument(s) (described further below) to assist the surgeon 201 during the procedure. A surgical microscope system 500 is supported at a distal end of a robotic arm of a positioning system 208. The surgical microscope system 500 is used to capture images, e.g., a static image or frames of a video, of the surgical site; and the captured images are displayed on one or more displays for viewing by the surgeon 201.

Still referring to FIG. 7, although the surgical microscope system 500 is shown as being used in the context of a navigation system environment 200, e.g., being controlled as part of the navigation system 205, the surgical microscope system 500 may also be used outside of a navigation system environment, e.g., without any navigation support.

Still referring to FIG. 7, the position and orientation of the surgical microscope system 500 is determined based on tracking by the navigation system 205 (if used) and/or based on the position and orientation of the positioning system 208 (if the surgical microscope system 500 is supported by the positioning system 208). The distance d between the surgical microscope system 500 (more specifically, the aperture of the surgical microscope system 500) and the viewing target, e.g., the surface of the surgical site, is referred to as the working distance. The surgical microscope system 500 is configured for use in a predefined range of working distance, e.g., in the range of approximately 15 cm to approximately 75 cm. If the surgical microscope system 500 is mounted on the positioning system 208, the actual available range of working distance is dependent on at least the working distance of the surgical microscope system 500 and the workspace and kinematics of the positioning system 208.

Figure 10:
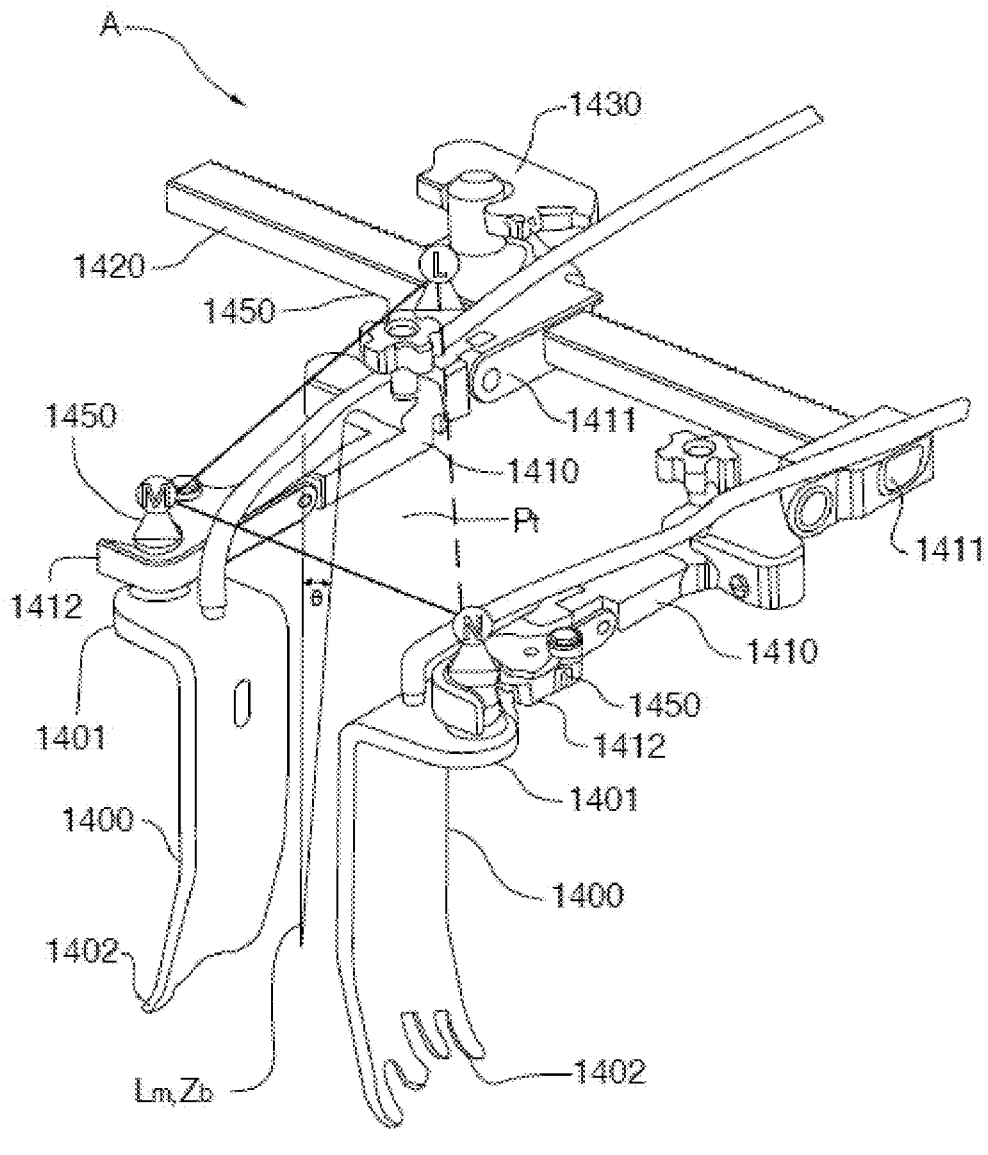
FIG. 10 is a diagram illustrating a perspective view of a trackable retractor apparatus, usable with the control and processing system, as shown in FIG. 4, during a medical procedure, such as a surgical procedure, as shown in FIG. 5, and an image-guided surgical procedure.

Referring to FIG. 10, this diagram illustrates, in a perspective view, a trackable retractor apparatus A, usable in an image-guided medical procedure, in accordance with an embodiment of the present disclosure. The trackable retractor apparatus A comprises: a pair of retractor blades 400, each retractor blade of the pair of retractor blades having a proximal end 401 and a distal end 402, the pair of retractor blades 400 having a blade axis $Z_b$ defined by a midline $L_m$ therebetween; a pair of actuation arms 410, each actuation arm 410 of the pair of actuation arms 410 having a proximal end 411 and a distal end 412, each actuation arm distal end 412 configured to correspondingly couple with each retractor blade proximal end 401, and each actuation arm 410 configured to correspondingly actuate each retractor blade 400 of the pair of retractor blades 400; a positioning arm 420 configured to position each actuation arm 410 of the pair of actuation arms 410; a movable clamp 430 configured to movably couple with the positioning arm 420 and one actuation arm 410 of the pair of actuation arms 410 and to move the one actuation arm 410 of the pair of actuation arms 410 relative to the other actuation arm 410 of the pair of actuation arms 410; and at least three distinct tracking features 440 disposed in a tracking plane $P_t$, at least two distinct tracking features 440 of the at least three distinct tracking features 440 configured to correspondingly couple with the retractor blade proximal ends 401, at least one other distinct tracking feature 440 of the plurality of distinct tracking features 440 configured to couple with the movable clamp 430, and each distinct tracking feature 440 of the plurality of distinct tracking features 440 comprising a distinct tracking token 450, whereby the blade axis $Z_b$ is maintained in a position orthogonal to the tracking plane $P_t$, and whereby optical alignment is maintained along the blade axis $Z_b$ in relation to a desired focal depth.

Still referring to FIG. 10, in the apparatus A, at least one distinct tracking feature 1440 of the at least three distinct tracking features 1440 further comprises a passive tracking marker (not shown), wherein the passive tracking marker comprises at least one of a reflective sphere (not shown) and a retroreflective sphere (not shown). Alternatively or additionally, at least one distinct tracking feature 1440 of the at least three distinct tracking features 1440 further comprises an active tracking marker (not shown), wherein the active tracking marker comprises a light-emitting diode (not shown).

Still referring to FIG. 10, in the apparatus A, the positioning arm 1420 is further configured to position to position the one actuation arm 1410 relative to the other actuation arm 1410 for disposing the pair of retractor blades 1400 in relation to the desired focal depth. Alternatively or additionally, the movable clamp 1430 is further configured to move the one actuation arm 1410 relative to the other actuation arm 1410 for disposing the pair of retractor blades 1400 in relation to the desired focal depth.

Still referring to FIG. 10, in the apparatus A, optionally, at least one of the positioning arm 1420 and the movable clamp 1430 is responsive to voice recognition. The movable clamp 1430 is further configured to move the one actuation arm 1410 relative to the other actuation arm 1410 by tilting the blade axis $Z_b$, e.g., at an angle θ, in relation to the desired focal depth. The movable clamp 1430 is further configured to move the one actuation arm 1410 relative to the other actuation arm 1410 by tilting the blade axis $Z_b$ in relation to the desired focal depth in response to voice recognition.

Referring to FIG. 11, this flow diagram illustrates a method M1 of providing a trackable retractor apparatus A, usable in an image-guided medical procedure, in accordance with an embodiment of the present disclosure. The method M1 comprises: providing a pair of retractor blades, providing the pair of retractor blades comprising providing each retractor blade of the pair of retractor blades having a proximal end and a distal end, and providing the pair of retractor blades comprising providing the pair of retractor blades having a blade axis defined by a midline therebetween, as indicated by block 5001; providing a pair of actuation arms, each actuation arm of the pair of actuation arms having a proximal end and a distal end, each actuation arm distal end correspondingly coupled with each retractor blade proximal end, and each actuation arm configured to correspondingly actuate each retractor blade of the pair of retractor blades, as indicated by block 5002; providing a positioning arm configured to position each actuation arm of the pair of actuation arms, as indicated by block 5003; providing a movable clamp configured to movably couple with the positioning arm and one actuation arm of the pair of actuation arms and to move the one actuation arm of the pair of actuation arms relative to the other actuation arm of the pair of actuation arms, as indicated by block 5004; and providing at least three distinct tracking features disposed in a tracking plane, providing the at least three distinct tracking features comprising configuring at least two distinct tracking features to correspondingly couple with the retractor blade proximal ends, providing the at least three distinct tracking features comprising configuring at least one other distinct tracking features of the plurality of distinct tracking features to couple with the movable clamp, and providing the at least three distinct tracking features comprising providing each distinct tracking feature of the plurality of distinct tracking features as a distinct tracking token, as indicated by block 5005, whereby the blade axis is maintained in a position orthogonal to the tracking plane, and whereby optical alignment is maintained along the blade axis in relation to a desired focal depth.

Still referring to FIG. 11, in the method M1, providing the at least three distinct tracking features further comprises providing at least one distinct tracking feature with a passive tracking marker, wherein providing the at least one distinct tracking feature with a passive tracking marker comprises providing at least one of a reflective sphere and a retrore-flective sphere. Alternatively or additionally, providing the at least three distinct tracking features further comprises providing at least one distinct tracking feature with an active tracking marker. Providing at least one distinct tracking feature with the active tracking marker comprises providing a light-emitting diode.

Still referring to FIG. 11, in the method M1, providing the positioning arm further configuring the positioning arm to position the one actuation arm relative to the other actuation arm for disposing the pair of retractor blades in relation to the desired focal depth. Alternatively or additionally, providing the movable clamp further configuring the movable clamp to move the one actuation arm relative to the other actuation arm for disposing the pair of retractor blades in relation to the desired focal depth.

Still referring to FIG. 11, in the method M1, at least one of providing the positioning arm and providing movable clamp respectively comprises providing the positioning arm and providing the movable clamp as responsive to voice recognition. Providing the movable clamp further comprises configuring the movable clamp to move the one actuation arm relative to the other actuation arm by tilting the blade axis in relation to the desired focal depth.

Referring to FIG. 12, this flow diagram illustrating a method M2 of maintaining optical alignment by way of a trackable retractor apparatus A, usable in an image-guided medical procedure, in accordance with an embodiment of the present disclosure. The method M2 comprises: providing the trackable retractor apparatus A, as indicated by block 6000, providing the apparatus A comprising: providing a pair of retractor blades, providing the pair of retractor blades comprising providing each retractor blade of the pair of retractor blades having a proximal end and a distal end, and providing the pair of retractor blades comprising providing the pair of retractor blades having a blade axis defined by a midline therebetween, as indicated by block 6001; providing a pair of actuation arms, each actuation arm of the pair of actuation arms having a proximal end and a distal end, each actuation arm distal end correspondingly coupled with each retractor blade proximal end, and each actuation arm configured to correspondingly actuate each retractor blade of the pair of retractor blades, as indicated by block 6002; providing a positioning arm configured to position each actuation arm of the pair of actuation arms, as indicated by block 6003; providing a movable clamp configured to movably couple with the positioning arm and one actuation arm of the pair of actuation arms and to move the one actuation arm of the pair of actuation arms relative to the other actuation arm of the pair of actuation arms, as indicated by block 6004; and providing at least three distinct tracking features disposed in a tracking plane, providing the at least three distinct tracking features comprising configuring at least two distinct tracking features to correspondingly couple with the retractor blade proximal ends, providing the at least three distinct tracking features comprising configuring at least one other distinct tracking features of the plurality of distinct tracking features to couple with the movable clamp, and providing the at least three distinct tracking features comprising providing each distinct tracking feature of the plurality of distinct tracking features as a distinct tracking token, as indicated by block 6005, whereby the blade axis is maintained in a position orthogonal to the tracking plane, and whereby optical alignment is maintained along the blade axis in relation to a desired focal depth; and operating the trackable retractor apparatus A, as indicated by block 6006.

Still referring to FIG. 12, in the method M2, providing the at least three distinct tracking features further comprises providing at least one distinct tracking feature with a passive tracking marker, wherein providing the at least one distinct tracking feature with a passive tracking marker comprises providing at least one of a reflective sphere and a retroreflective sphere. Alternatively or additionally, providing the at least three distinct tracking features further comprises providing at least one distinct tracking feature with an active tracking marker. Providing at least one distinct tracking feature with the active tracking marker comprises providing a light-emitting diode.

Still referring to FIG. 12, in the method M2, providing the positioning arm further configuring the positioning arm to position the one actuation arm relative to the other actuation arm for disposing the pair of retractor blades in relation to the desired focal depth. Alternatively or additionally, providing the movable clamp further configuring the movable clamp to move the one actuation arm relative to the other actuation arm for disposing the pair of retractor blades in relation to the desired focal depth.

Still referring to FIG. 12, in the method M2, at least one of providing the positioning arm and providing movable clamp respectively comprises providing the positioning arm and providing the movable clamp as responsive to voice recognition. Providing the movable clamp further comprises configuring the movable clamp to move the one actuation arm relative to the other actuation arm by tilting the blade axis in relation to the desired focal depth.

Although the present disclosure describes methods and processes with steps in a certain order, one or more steps of the methods and processes may be omitted or altered as appropriate. One or more steps may take place in an order other than that in which they are described, as appropriate. In many cases the order of process steps may be varied without changing the purpose, effect, or import of the methods described.

Although the present disclosure is described, at least in part, in terms of methods, a person of ordinary skill in the art will understand that the present disclosure is also directed to the various components for performing at least some of the aspects and features of the described methods, be it by way of hardware components, software or any combination of the two. Accordingly, the technical solution of the present disclosure may be embodied in the form of a software product. The software product includes instructions tangibly stored thereon that enable a processing device, e.g., a personal computer, a server, or a network device, to execute examples of the methods herein disclosed.

At least some aspects disclosed may be embodied, at least in part, in software. That is, some disclosed techniques and methods may be carried out in a computer system or other data processing system in response to its processor, such as a microprocessor, executing sequences of instructions contained in a memory, such as read only memory (ROM), volatile random access memory (RAM), non-volatile memory, cache or a remote storage device.

A computer-readable storage medium may be used to store software and data which when executed by a data processing system causes the system to perform various methods or techniques of the present disclosure. The executable software and data may be stored in various places including for example ROM, volatile RAM, non-volatile memory and/or cache. Portions of this software and/or data may be stored in any one of these storage devices.

Examples of computer-readable storage media may include, but are not limited to, recordable and non-recordable type media such as volatile and non-volatile memory devices, ROM, RAM, flash memory devices, floppy and other removable disks, magnetic disk storage media, optical storage media, e.g., compact discs (CDs), digital versatile disks (DVDs), etc., among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Furthermore, at least some of the methods herein described may be capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

At least some of the elements of the systems herein described may be implemented by software, or a combination of software and hardware. Elements of the system that are implemented via software may be written in any suitable programming language and may comprise software modules or engines, for example. Software instructions may be stored on storage media or on a computer readable medium that is readable by any suitable general or special purpose processing device, such as a processor. The processor may implement an operating system and may include any hardware and/or software that is necessary to implement the functionality of at least one of the embodiments herein described.

While some embodiments or aspects of the present disclosure may be implemented in fully functioning computers and computer systems, other embodiments or aspects may be capable of being distributed as a computing product in a variety of forms and may be capable of being applied regardless of the particular type of machine or computer readable media used to actually effect the distribution.

All values and sub-ranges within disclosed ranges are also disclosed. Also, although the systems, devices and processes disclosed and shown herein may comprise a specific number of elements/components, the systems, devices and assemblies could be modified to include additional or fewer of such elements/components. For example, although any of the elements/components disclosed may be referenced as being singular, the embodiments herein disclosed could be modified to include a plurality of such elements/components. The subject matter herein described intends to cover and embrace all suitable changes in technology.

While the teachings herein described are in conjunction with various embodiments for illustrative purposes, it is not intended that the teachings be limited to such embodiments. On the contrary, the teachings described and illustrated herein encompass various alternatives, modifications, and equivalents, without departing from the described embodiments. Selected features from one or more of the above-described embodiments may be combined to create alternative embodiments not explicitly described, features suitable for such combinations being understood within the scope of this disclosure.

Although the above discussion refers to the surgeon as being the user who controls and uses the examples of the present disclosure, the present disclosure is not limited to any specific user. In some examples, there may be a plurality of users involved. While some embodiments or aspects of the present disclosure may be implemented in fully functioning computers and computer systems, other embodiments or aspects may be capable of being distributed as a computing product in a variety of forms and may be capable of being applied regardless of the particular type of machine or computer readable media used to actually effect the distribution.

At least some aspects disclosed may be embodied, at least in part, in software. That is, some disclosed techniques and methods may be carried out in a computer system or other data processing system in response to its processor, such as a microprocessor, executing sequences of instructions contained in a memory, such as ROM, volatile RAM, non-volatile memory, cache or a remote storage device.

A computer readable storage medium may be used to store software and data which when executed by a data processing system causes the system to perform various methods or techniques of the present disclosure. The executable software and data may be stored in various places including for example ROM, volatile RAM, non-volatile memory and/or cache. Portions of this software and/or data may be stored in any one of these storage devices.

Examples of computer-readable storage media comprises, but are not limited to, recordable and non-recordable type media such as volatile and non-volatile memory devices, read only memory (ROM), random access memory (RAM), flash memory devices, floppy and other removable disks, magnetic disk storage media, optical storage media, e.g., compact discs (CDs), digital versatile disks (DVDs), etc., among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Furthermore, at least some of the methods herein described may be capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

At least some of the elements of the systems herein described may be implemented by software, or a combination of software and hardware. Elements of the system that are implemented via software may be written in a high-level procedural language such as object oriented programming or a scripting language. Accordingly, the program code may be written in C, C++, J++, or any other suitable programming language and may comprise modules or classes, as in object oriented programming. At least some of the elements of the system that are implemented via software may be written in assembly language, machine language or firmware as needed. In either case, the program code can be stored on storage media or on a computer readable medium that is readable by a general or special purpose programmable computing device having a processor, an operating system and the associated hardware and software that is necessary to implement the functionality of at least one of the embodiments herein described. The program code, when read by the computing device, configures the computing device to operate in a new, specific and predefined manner in order to perform at least one of the methods herein described.

While the teachings herein described are in conjunction with various embodiments for illustrative purposes, it is not intended that the teachings be limited to such embodiments. On the contrary, the teachings described and illustrated herein encompass various alternatives, modifications, and equivalents, without departing from the described embodiments, the general scope of which is defined in the appended claims. Except to the extent necessary or inherent in the processes themselves, no particular order to steps or stages of methods or processes described in this disclosure is intended or implied. In many cases, the order of process steps may be varied without changing the purpose, effect, or import of the methods described.

Information, as herein shown and described in detail, is fully capable of attaining the above-described embodiments of the present disclosure as well as the presently preferred embodiment of the present disclosure, and is, thus, representative of the subject matter which is broadly contemplated by the present disclosure. The scope of the present disclosure fully encompasses other embodiments; and the claims are not limited by anything other than their subject matter, wherein any reference to an element being made in the singular is not intended to denote "one and only one" unless explicitly so stated, but, rather to denote "at least one" or "one or more." All structural and functional equivalents to the elements of the above-described preferred embodiment and additional embodiments as regarded by those of ordinary skill in the art are hereby expressly incorporated by reference and are intended to be encompassed by the present claims.

Moreover, no requirement exists for a system or method to address each and every problem sought to be resolved by the present disclosure, for such to be encompassed by the present claims. Furthermore, no element, component, or method step in the present disclosure is intended to be dedicated to the public, regardless of whether the element, component, or method step is explicitly recited in the claims. However, that various changes and modifications in form, material, work-piece, and fabrication material detail may be made, without departing from the spirit and scope of the present disclosure, and are also encompassed by the present disclosure. In addition, any combination or permutation of any feature, as herein explicitly and/or implicitly disclosed, is also encompassed by the present disclosure.

What is claimed:

1. A trackable retractor apparatus, configured to support a surgical navigation system during a surgical navigation medical procedure, the apparatus comprising:

a pair of retractor blades, each retractor blade of the pair of retractor blades having a proximal end and a distal end, the pair of retractor blades having a blade axis defined by a midline therebetween;

a pair of actuation arms, each actuation arm of the pair of actuation arms having a proximal end and a distal end, each actuation arm distal end configured to correspondingly couple with each retractor blade proximal end, and each actuation arm configured to correspondingly actuate each retractor blade of the pair of retractor blades;

a positioning arm configured to position each actuation arm of the pair of actuation arms;

a movable clamp configured to movably couple with the positioning arm and one actuation arm of the pair of actuation arms and to move the one actuation arm of the pair of actuation arms relative to the other actuation arm of the pair of actuation arms; and at least three distinct tracking features disposed in a tracking plane, at least two distinct tracking features of the at least three distinct tracking features configured to correspondingly couple with the retractor blade proximal ends, at least one other distinct tracking feature of the plurality of distinct tracking features configured to couple with the movable clamp, and each distinct tracking feature of the plurality of distinct tracking features comprising a distinct tracking token, whereby the blade axis is maintained in a position orthogonal to the tracking plane, and whereby optical alignment is maintained along the blade axis in relation to a desired focal depth;

wherein the at least one other distinct tracking feature further comprises a passive tracking marker or an active tracking marker;

wherein the passive tracking marker comprises at least one of a reflective sphere and a retroreflective sphere; and wherein the active tracking marker comprises a light-emitting diode.

2. The apparatus of claim 1, wherein at least one of:

the positioning arm is further configured to position to position the one actuation arm relative to the other actuation arm for disposing the pair of retractor blades in relation to the desired focal depth, and the movable clamp is further configured to move the one actuation arm relative to the other actuation arm for disposing the pair of retractor blades in relation to the desired focal depth.

3. The apparatus of claim 2, wherein the movable clamp is further configured to move the one actuation arm relative to the other actuation arm by tilting the blade axis in relation to the desired focal depth.

4. The apparatus of claim 3, wherein the movable clamp is further configured to move the one actuation arm relative to the other actuation arm by tilting the blade axis in relation to the desired focal depth in response to voice recognition.

5. The apparatus of claim 1, wherein at least one of the positioning arm and the movable clamp is responsive to voice recognition.

6. The apparatus of claim 1, wherein at least one distinct tracking feature of the at least three distinct tracking features further comprises at least one of a passive tracking marker and an active tracking marker, wherein the passive tracking marker comprises at least one of a reflective sphere and a retroreflective sphere, wherein the active tracking marker comprises a light-emitting diode, wherein at least one of:

the positioning arm is further configured to position the one actuation arm relative to the other actuation arm for disposing the pair of retractor blades in relation to the desired focal depth, and

the movable clamp is further configured to move the one actuation arm relative to the other actuation arm for disposing the pair of retractor blades in relation to the desired focal depth, wherein at least one of the positioning arm and the movable clamp is responsive to voice recognition, and;

wherein the movable clamp is further configured to move the one actuation arm relative to the other actuation arm by tilting the blade axis in relation to the desired focal depth.

7. The method of claim 1, wherein providing the at least three distinct tracking features comprises providing at least one distinct tracking feature as at least one of a passive tracking marker and an active tracking marker, wherein providing the passive tracking marker comprises providing at least one of a reflective sphere and a retroreflective sphere, wherein providing at least one distinct tracking feature as the active tracking marker comprises providing a light-emitting diode, wherein at least one of:

providing the positioning arm further configuring the positioning arm to position the one actuation arm relative to the other actuation arm for disposing the pair of retractor blades in relation to the desired focal depth, and providing the movable clamp further configuring the movable clamp to move the one actuation arm relative to the other actuation arm for disposing the pair of retractor blades in relation to the desired focal depth, wherein at least one of providing the positioning arm and providing movable clamp respectively comprises providing the positioning arm and providing the movable clamp as responsive to voice recognition, and wherein providing the movable clamp further comprises configuring the movable clamp to move the one actuation arm relative to the other actuation arm by tilting the blade axis in relation to the desired focal depth.

8. A method of providing a trackable retractor apparatus, the apparatus configured to support a surgical navigation system during a surgical navigation medical procedure, the method comprising:

providing a pair of retractor blades, providing the pair of retractor blades comprising providing each retractor blade of the pair of retractor blades having a proximal end and a distal end, and providing the pair of retractor blades comprising providing the pair of retractor blades having a blade axis defined by a midline therebetween;

providing a pair of actuation arms, each actuation arm of the pair of actuation arms having a proximal end and a distal end, each actuation arm distal end correspondingly coupled with each retractor blade proximal end, and each actuation arm configured to correspondingly actuate each retractor blade of the pair of retractor blades;

providing a positioning arm configured to position each actuation arm of the pair of actuation arms;

providing a movable clamp configured to movably couple with the positioning arm and one actuation arm of the pair of actuation arms and to move the one actuation arm of the pair of actuation arms relative to the other actuation arm of the pair of actuation arms; and providing at least three distinct tracking features disposed in a tracking plane, providing the at least three distinct tracking features comprising configuring at least two distinct tracking features to correspondingly couple with the retractor blade proximal ends, providing the at least three distinct tracking features comprising configuring at least one other distinct tracking features of the plurality of distinct tracking features to couple with the movable clamp, and providing the at least three distinct tracking features comprising providing each distinct tracking feature of the plurality of distinct tracking features as a distinct tracking token, whereby the blade axis is maintained in a position orthogonal to the tracking plane, and whereby optical alignment is maintained along the blade axis in relation to a desired focal depth; wherein the at least one other distinct tracking feature further comprises a passive tracking marker or an active tracking marker;

wherein the passive tracking marker comprises at least one of a reflective sphere and a retroreflective sphere; and wherein the active tracking marker comprises a light-emitting diode.

9. The method of claim 8, wherein at least one of:

providing the positioning arm further configuring the positioning arm to position the one actuation arm relative to the other actuation arm for disposing the pair of retractor blades in relation to the desired focal depth, and providing the movable clamp further configuring the movable clamp to move the one actuation arm relative to the other actuation arm for disposing the pair of retractor blades in relation to the desired focal depth.

10. The method of claim 9, wherein at least one of providing the positioning arm and providing movable clamp respectively comprises providing the positioning arm and providing the movable clamp as responsive to voice recognition.

11. The method of claim 8, wherein providing the movable clamp further comprises configuring the movable clamp to move the one actuation arm relative to the other actuation arm by tilting the blade axis in relation to the desired focal depth.

12. A method of maintaining optical alignment by way of a trackable retractor apparatus, the apparatus configured to support a surgical navigation system during a surgical navigation medical procedure, the method comprising:

providing the trackable retractor apparatus, providing the apparatus comprising:

providing a pair of retractor blades, providing the pair of retractor blades comprising providing each retractor blade of the pair of retractor blades having a proximal end and a distal end, and providing the pair of retractor blades comprising providing the pair of retractor blades having a blade axis defined by a midline therebetween;

providing a pair of actuation arms, each actuation arm of the pair of actuation arms having a proximal end and a distal end, each actuation arm distal end correspondingly coupled with each retractor blade proximal end, and each actuation arm configured to correspondingly actuate each retractor blade of the pair of retractor blades;

providing a positioning arm configured to position each actuation arm of the pair of actuation arms;

providing a movable clamp configured to movably couple with the positioning arm and one actuation arm of the pair of actuation arms and to move the one actuation arm of the pair of actuation arms relative to the other actuation arm of the pair of actuation arms; and providing at least three distinct tracking features disposed in a tracking plane, providing the at least three distinct tracking features comprising configuring at least two distinct tracking features to correspondingly couple with the retractor blade proximal ends, providing the at least three distinct tracking features comprising configuring at least one other distinct tracking features of the plurality of distinct tracking features to couple with the movable clamp, and providing the at least three distinct tracking features comprising providing each distinct tracking feature of the plurality of distinct tracking features as a distinct tracking token, whereby the blade axis is maintained in a position orthogonal to the tracking plane, and whereby optical alignment is maintained along the blade axis in relation to a desired focal depth; and operating the trackable retractor apparatus;

wherein the least one other distinct tracking feature further comprises a passive tracking marker or an active tracking marker;

wherein the passive tracking marker comprises at least one of a reflective sphere and a retroreflective sphere; and wherein the active tracking marker comprises a light-emitting diode.

* * * * *